United States Patent
Goto et al.

(10) Patent No.: US 8,175,364 B2
(45) Date of Patent: May 8, 2012

(54) MEDICAL IMAGE DISPLAY DEVICE AND PROGRAM THAT GENERATES MARKER AND CHANGES SHAPE OF REGION OF INTEREST TO CONTACT MARKER

(75) Inventors: Yoshihiro Goto, Tokyo (JP); Yudai Ogawa, Chiba (JP); Osamu Sasahara, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 736 days.

(21) Appl. No.: 12/300,143

(22) PCT Filed: May 16, 2007

(86) PCT No.: PCT/JP2007/060037
§ 371 (c)(1),
(2), (4) Date: Nov. 10, 2008

(87) PCT Pub. No.: WO2007/135913
PCT Pub. Date: Nov. 29, 2007

(65) Prior Publication Data
US 2009/0116718 A1    May 7, 2009

(30) Foreign Application Priority Data

May 19, 2006 (JP) ................................ 2006-140561
May 24, 2006 (JP) ................................ 2006-143782

(51) Int. Cl.
*G06K 9/00* (2006.01)
(52) U.S. Cl. ........................................ 382/131; 382/128

(58) Field of Classification Search .................... None
See application file for complete search history.

(56) References Cited

U.S. PATENT DOCUMENTS

| 5,479,591 | A | * | 12/1995 | Goto | 345/627 |
| 7,221,787 | B2 | * | 5/2007 | Luo et al. | 382/132 |
| 7,251,363 | B2 | * | 7/2007 | Priddy | 382/173 |

FOREIGN PATENT DOCUMENTS

| JP | 7-175942 | | 7/1995 |
| JP | 2000-163555 | | 6/2000 |
| JP | 2000-163581 | | 6/2000 |
| JP | 2000-163599 | | 6/2000 |
| JP | 2000-172391 | | 6/2000 |
| JP | 2001-22916 | | 1/2001 |
| JP | 2005-28051 | | 2/2005 |
| JP | 2005-028051 | * | 2/2005 |
| JP | 2005-73817 | | 3/2005 |

* cited by examiner

*Primary Examiner* — Vinh Nguyen
(74) *Attorney, Agent, or Firm* — Cooper & Dunham LLP

(57) ABSTRACT

A medical image display device is configured to set first reference information for starting extraction of a desired region on a medical image displayed on a display and second reference information for terminating the region extraction, generate a marker with finite size indicating execution information on a region extraction process in the direction from the first reference information to the second reference information, and control display of the marker and a region of interest on the display by associating it with the medical image. For example, the marker is shifted and set, and the shape of the region of interest is changed so as to contact the marker after being shifted.

15 Claims, 19 Drawing Sheets

FIG.5
(A)
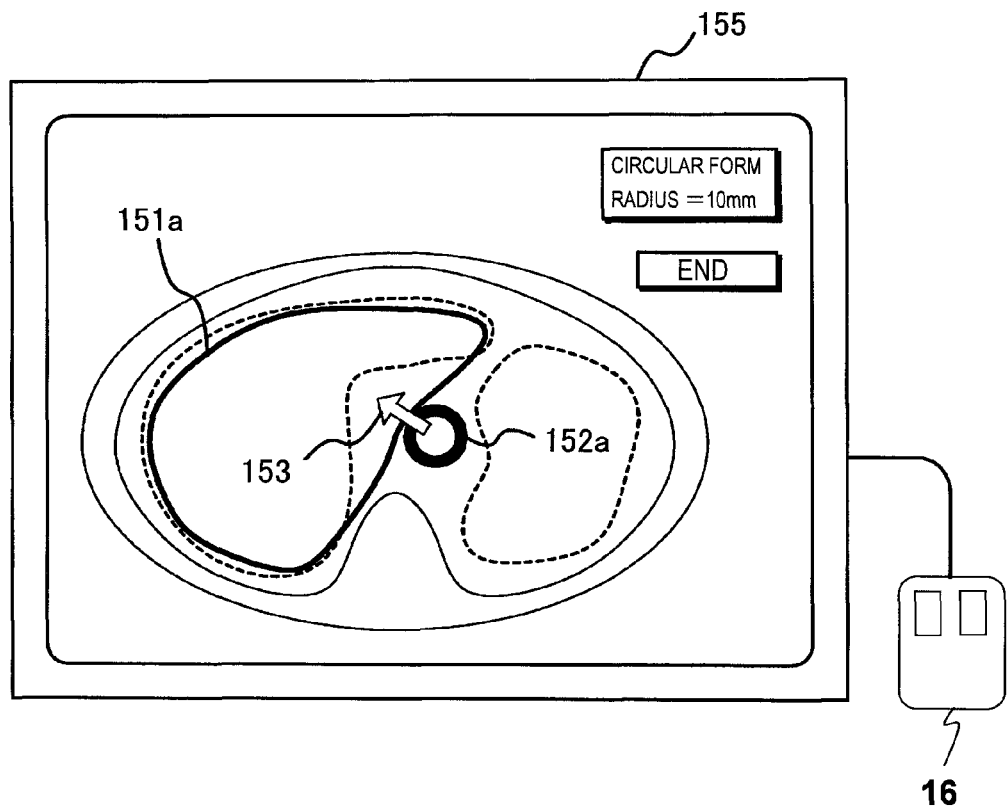
(B)
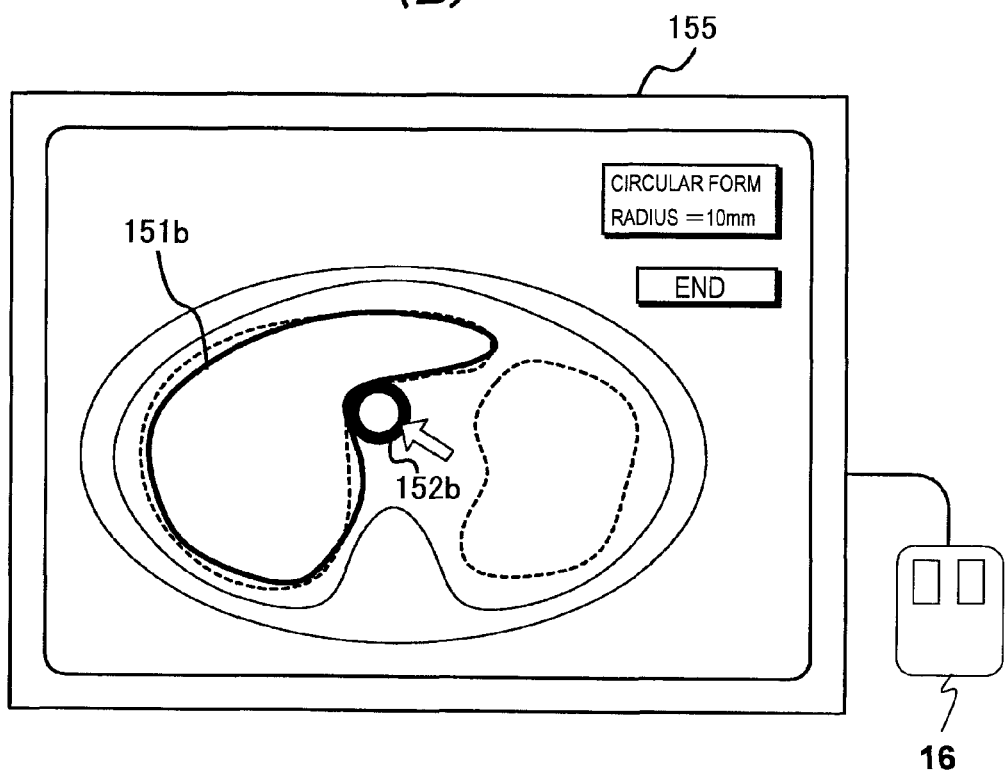

FIG.6
(A)
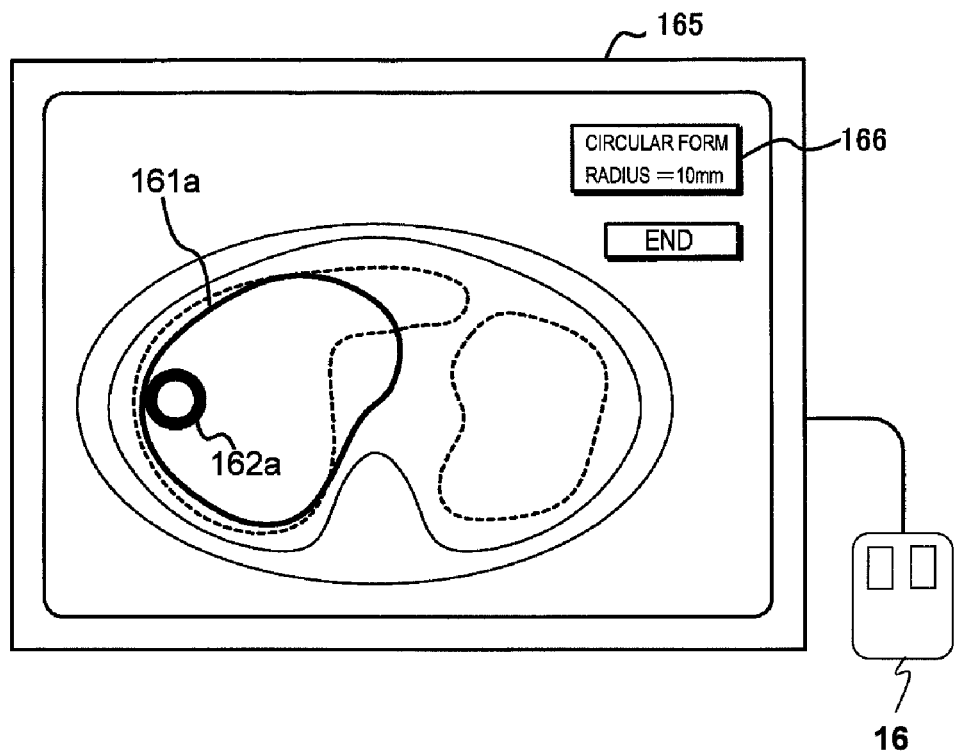
(B)
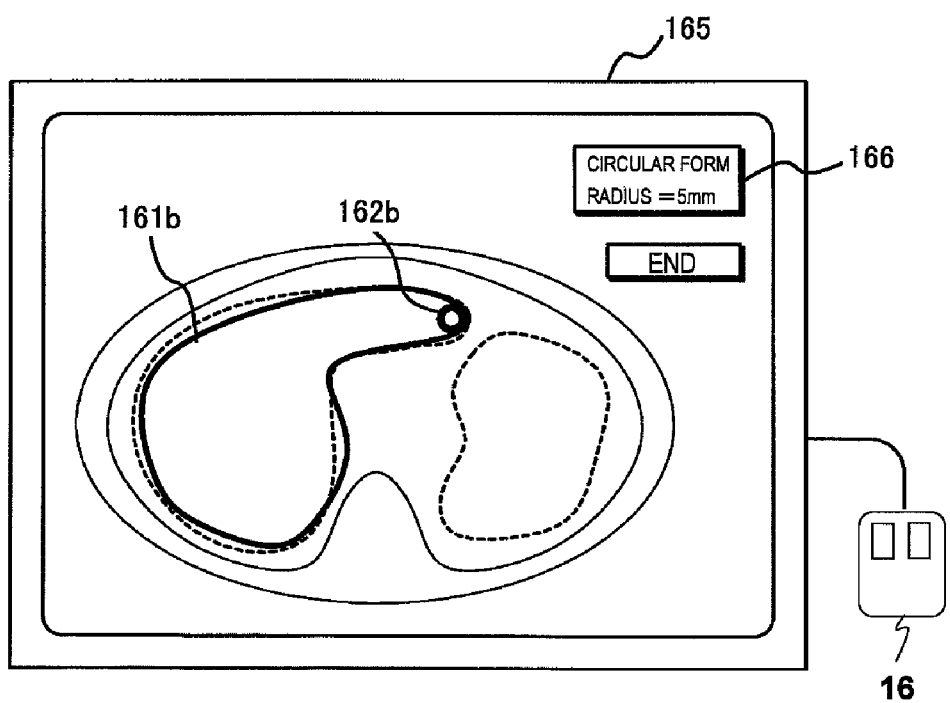

WHEN ONE PIXEL IS ADDED (/DELETED)

WHEN ONE PIXEL IS ADDED (/DELETED)

WHEN TWO PIXELS ARE ADDED (/DELETED)

FIG.12
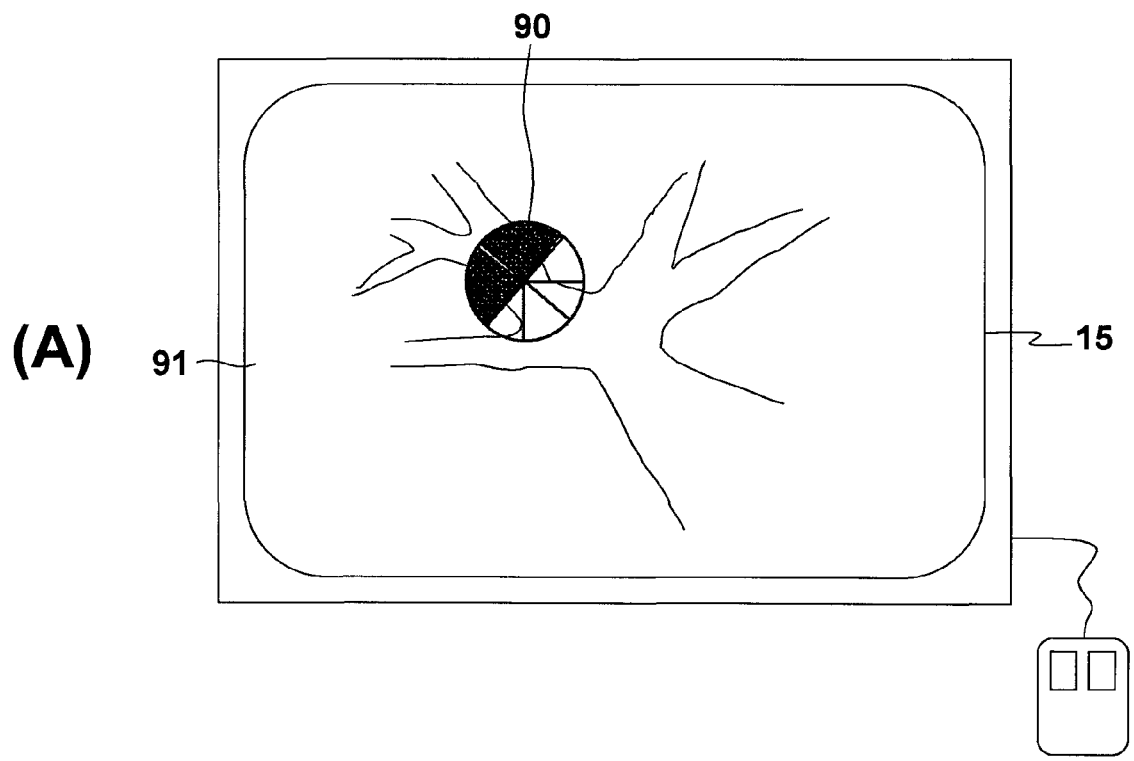
(A)
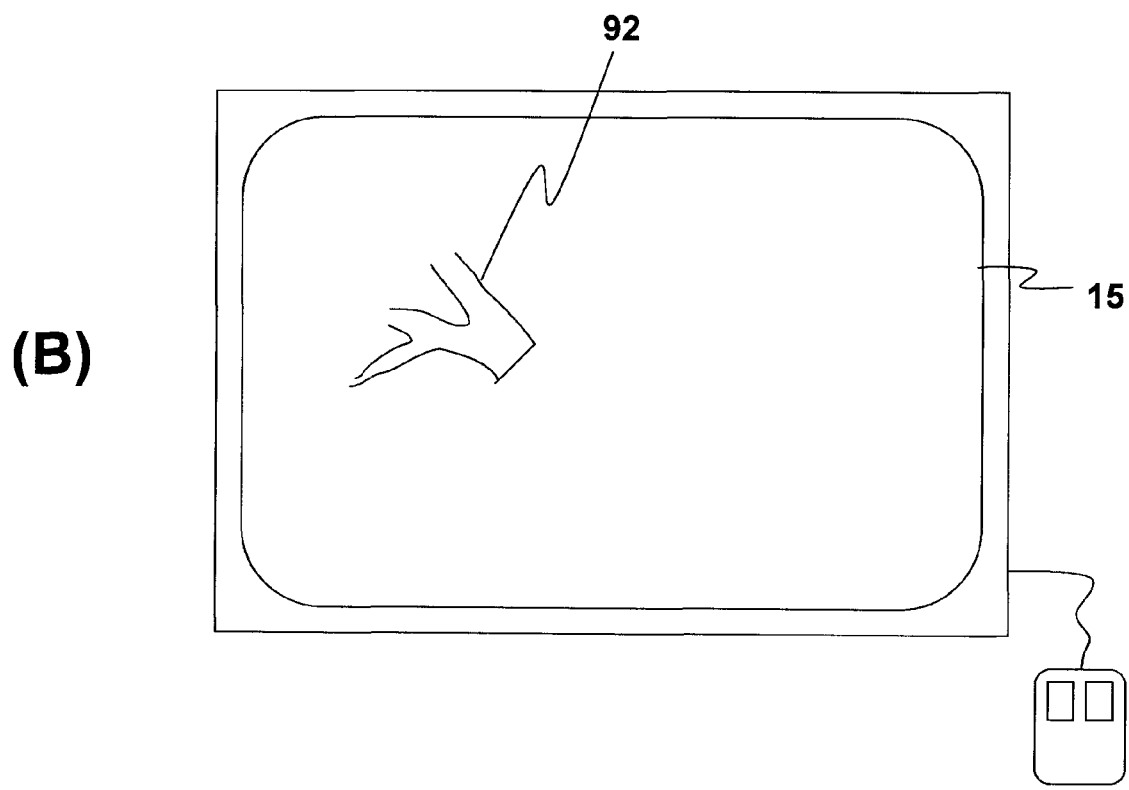
(B)

MEDICAL IMAGE DISPLAY DEVICE AND PROGRAM THAT GENERATES MARKER AND CHANGES SHAPE OF REGION OF INTEREST TO CONTACT MARKER

TECHNICAL FIELD

The present invention is related to a medical image display device and program for displaying medical images including CT images and MR images, in particular to a technique for extracting a predetermined region such as an organ.

TECHNICAL BACKGROUND

In medical images, there are mixed imaging regions corresponding to many areas of an object to be examined such as organs, muscles, fat and bones (hereinafter generically referred to as "organs, etc."). In such medical images, when a doctor desires to obtain a 3-dimensional image by extracting, for example, only the region showing a liver, there is a method referred to as the region extracting process for extracting only the liver region.

The conventional region extracting process is executed using the region growing method or the threshold value processing method. The region growing method is executed by the following procedure:

(1) An operator selects a region for extracting such as an organ, etc. from the medical image displayed on a screen, and specifies and inputs a point (1~several pixels) using a mouse on the selected region.

(2) A computer ultimately extracts the entire region of the desired organ, etc. while expanding one point in the region, applying the fact that the pixel value of the surrounding points of the one point in the region of the organ specified by the operator is constant or varies only a slight amount.

However, the region growing method has the problem that excessive region gets extracted in the case that the region that satisfies the extracting condition is arranged adjacent to the desired region, which requires the measures disclosed in Patent Document 1 to be taken.

Patent Document 1 discloses the method for adding restriction on the region expansion by implementing the region growing process only in the region where a region of interest is encompassed and set by a closed curve on a medical image.

Patent Document 1: JP-A-H10-192256

However, the conventional restriction method for region expansion has an unsolved problem that the operator is required to perform a complex operation to accurately encompass the region with a closed curve.

BRIEF SUMMARY

In an aspect of this disclosure there is provided a medical image display device and program capable of controlling the region extracting process by a simple operation.

In another aspect of this disclosure there is provided a medical image display device comprising:

setting means (16, 16a) for setting first reference information for starting extraction of a desired region on a medical image displayed on display means (14, 15) and second reference information for terminating the region extraction; and control means (11) for generating marking information indicating execution information of a region extraction process in the direction from the first reference information to the second reference information set by the setting means (16, 16a) and controlling display of the generated marking information on the display means (14, 15) by correlating it with the medical image.

In another aspect pf this disclosure there is provided a medical image display program of executable instructions that cause a computer to perform:

a function for setting first reference information for starting extraction of the desired region on a medical image displayed on a monitor (15) and second reference information for terminating the region extraction; and a function for generating mark information indicating execution information of the region extracting process in the direction from the set first reference information to the second reference information, and controlling display of the generated mark information on the monitor (15) by correlating it with the medical image.

Thus, it is possible to provide a medical image display device and program capable of controlling region extracting process by simple operation.

BRIEF DESCRIPTION OF THE DIAGRAMS

FIG. 5 show a display example of a processing pattern different from FIG. 3 and FIG. 4.

FIG. 6 show a display pattern of a marker different from FIG. 3~FIG. 5.

FIG. 12 is a pattern diagram showing an example of the result of processing in FIG. 11.

DESCRIPTION OF SYMBOLS

11 . . . CPU, 14 . . . display memory, 15 . . . monitor, 16 . . . mouse, 16a . . . controller.

BEST MODE FOR CARRYING OUT THE INVENTION

Hereinafter, the best mode for carrying out the present invention will be described using the attached diagrams. In all of the diagrams for illustrating embodiments of the present invention, the same symbols are appended to those having the same function, and the repeated explanation thereof will be omitted.

<System Configuration>

Figure 1:
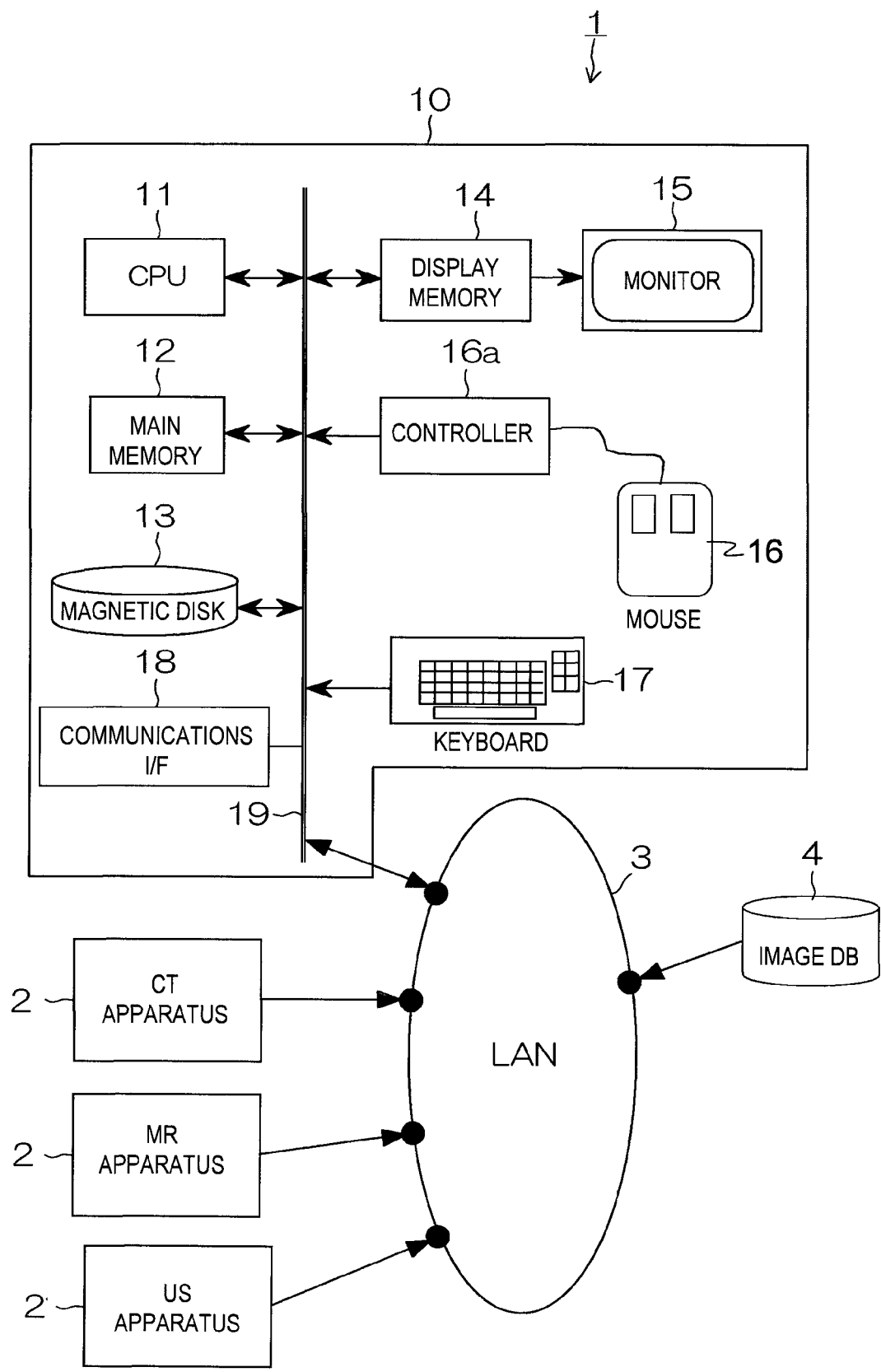
FIG. 1 shows an example of hardware configuration of the medical image display device related to the present embodiment.

FIG. 1 shows an example of hardware configuration of a medical image display device related to the present embodiment.

A medical image display system 1 comprises a medical imaging apparatus 2, image database (image DB) 4 and image display device 10 that are connected to a network such as LAN 3. The medical imaging apparatus 2 is for imaging an object to be examined, which can be any apparatus capable of imaging the object, without being limited to the exemplified X-ray CT apparatus, MRI apparatus and US apparatus. The image DB 4 accumulates medical images imaged by the medical imaging apparatus 2. The image display device 10 is for displaying an image of the object. Detailed configuration of the image display device 10 will be described as follows.

The image display device 10 comprises a central processing unit (CPU) 11, a main memory 12, a magnetic disk 13, a display memory 15, a controller 16a, a keyboard 17 and a communications interface (hereinafter referred to as "communications I/F") 18 connected to a bus 19 respectively. Also, a monitor 15 is connected to the display memory 14 and a mouse 16 is connected to the controller 16a.

Main function of the CPU 11 is to control operation of the respective components. The main memory 12 is a storing unit for storing the control program of the apparatus or to be an operating region upon executing the program. The magnetic disk 13 is an external storing unit for storing an operating system (OS), a device drive of the surrounding equipment or a variety of application software, etc. including a program for setting a processing direction on a medical image.

While only the magnetic disk 13 is connected as an external storing unit here, other devices such as a floppy disk drive, hard disk drive, CD-ROM drive, optical magnetic disk (MO) drive, ZIP drive, PD drive, DVD drive or USB memory may be connected. The display memory 14 is a memory for storing display data temporally. The monitor 15 is for displaying images on the basis of data temporally stored in the display memory 14 such as CRT monitor or liquid crystal monitor.

The mouse 16 is an example of a device for performing positional input to the image displayed on the monitor 15. The controller 16a is for detecting the position of the mouse 16 and outputting the position of a mouse pointer on the monitor 15 or a signal such as condition of the mouse 16 to the CPU 11. The keyboard 17 is an example of a device for inputting numbers and letters such as display condition of the image display device. The communications I/F 18 is for transmitting/receiving data between an external apparatus connected via LAN 3 such as obtaining medical images from the medical imaging apparatus 2. The bus 19 is a data transfer bus prepared for transmitting/receiving data among components connected to the CPU 11 such as the main memory 12 by the command from the CPU 11. The CPU 11 of an image display device 10 is for reading out the above-described imaging programs from the magnetic disk 13 to the main memory 12 so as to execute the programs thereof.

<Program Execution Example 1>

Next, operation of the medical image display apparatus will be described referring to FIG. 2~FIG. 5.

Figure 2:
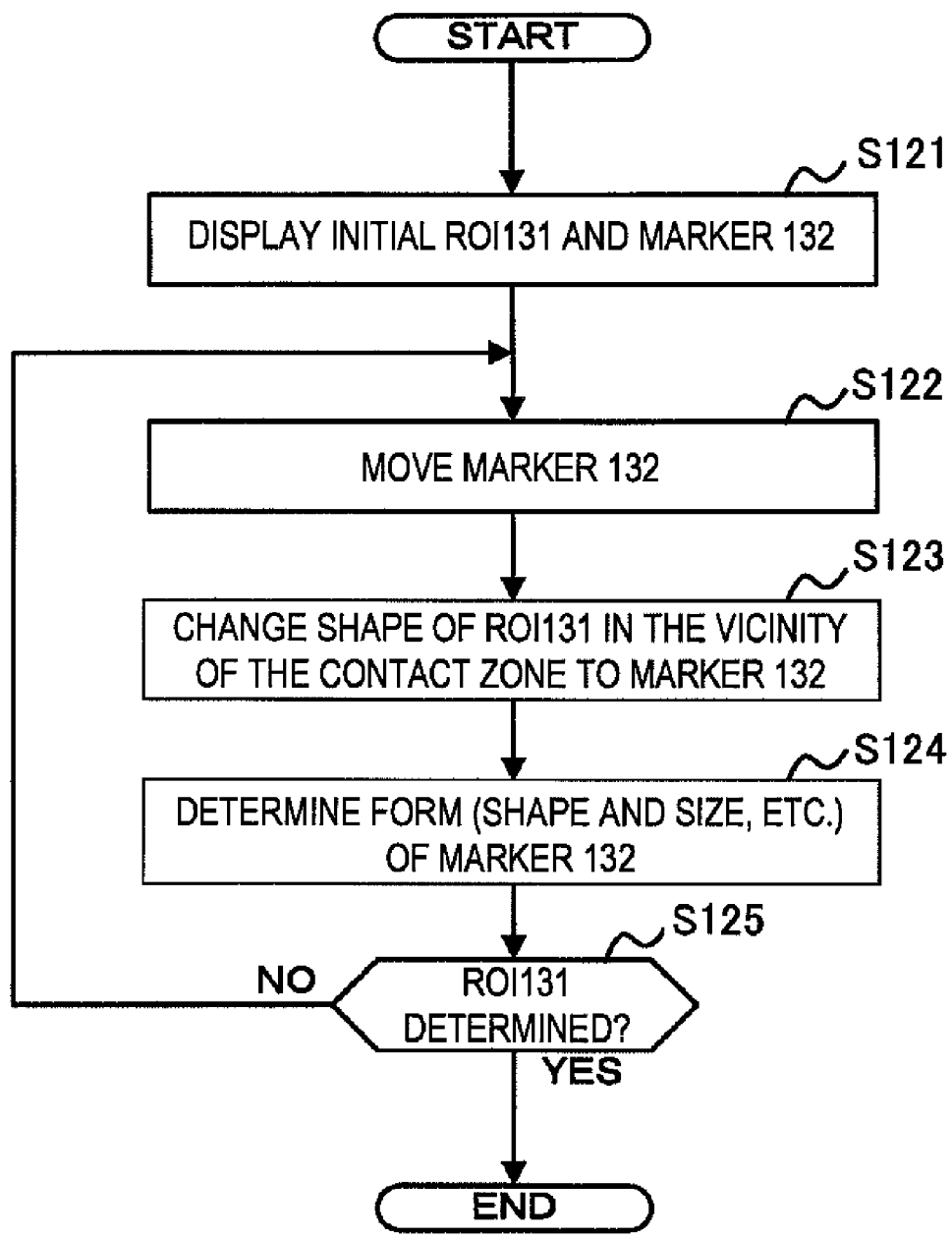
FIG. 2 shows a flow chart showing an operation example of a first embodiment of the medical image display device related to the present invention.
Figure 3:
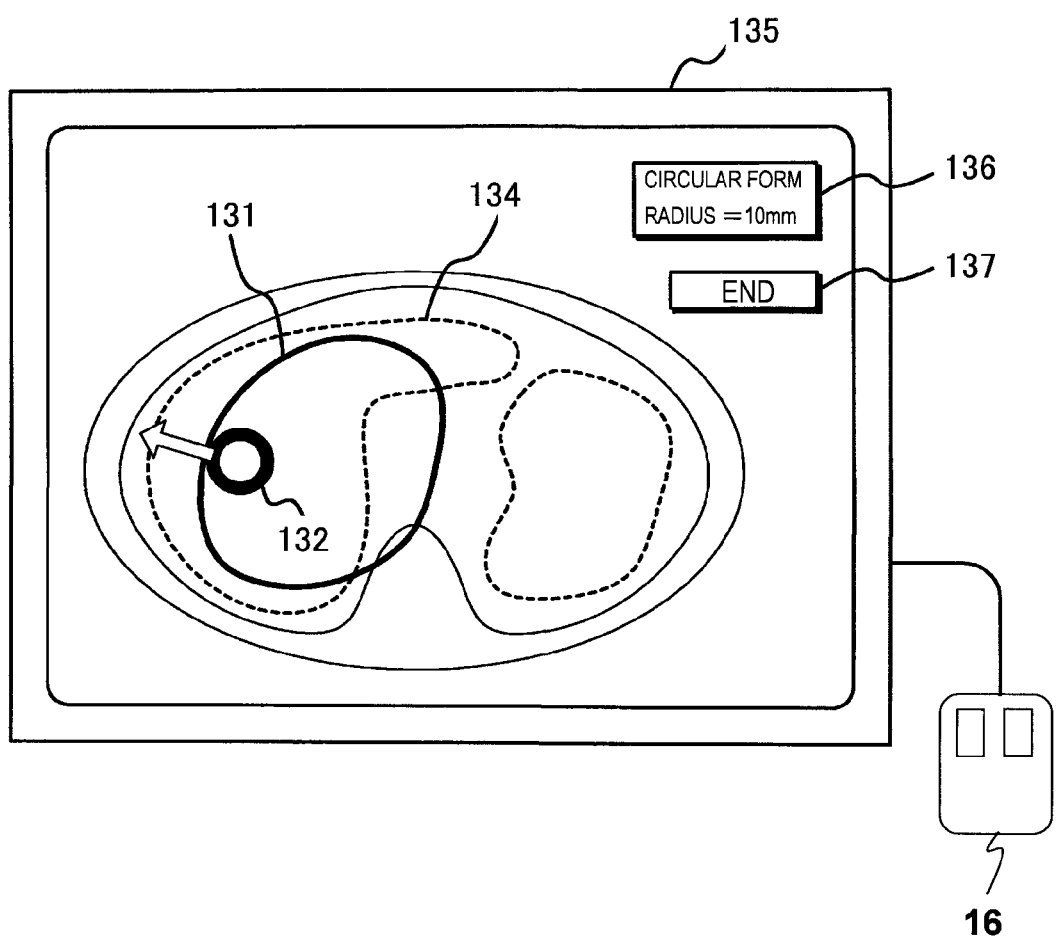
FIG. 3 shows a display example of an initial image of the processing in FIG. 2.

FIG. 2 is a flow chart of an operation example of the first embodiment of the medical image display device, and FIG. 3 shows a display example of an initial image of the processing in FIG. 2 illustrating a display screen 135 on which an ROI 131 and a marker 132 are displayed.

The CPU 11 displays the initial ROI 131 and the marker 132 (step S121). The ROI 131 and the marker 132 contact each other at least at one point. As for the form (shape and size, etc.) and the position of the initial ROI 131, the operator may draw it based on an organ contour 134 on the display screen 135, or it may be displayed by the CPU 11 on the basis of a default setting.

As for the form (shape and size, etc.) of the marker 132, it may be specified by the operator or displayed by the CPU 11 on the basis of the default setting. For example, the operator specifies the form of the marker 132 by pushing down a button 136 using the mouse 16.

Also, it may be set so that the form of the marker 132 is to be automatically determined based on the positional relationship between the ROI 131 and the marker 132 or the form of the ROI 131, by detecting the position of the marker 132 being specified by the operator via the CPU 11.

The operator shifts the marker 132 by dragging the mouse 16 and the CPU 11 displays the marker 132 after being shifted (step S122).

The CPU 11 changes the shape and displays the ROI 131 so as to contact the marker 132 after being shifted, in the vicinity of the contact zone of the ROI 131 and the marker 132 (step S123).

The CPU 11 determines and displays the form of the marker 132 based on the positional relationship between the ROI 131 and the marker 132 or the form of the ROI 131 in the vicinity of the contact zone (step S124).

The form of the marker 132 may be constant without changing.

The operator confirms whether the ROI 131 and the organ contour 134 are conformed or not. When the ROI 131 is determined ("YES" in step S125), the operator ends the process by pushing down the button 137 using the mouse 16. In the case to continue changing shape of the ROI 131 ("NO" in step S125), the CPU 11 repeats the process from step S122.

Figure 4:
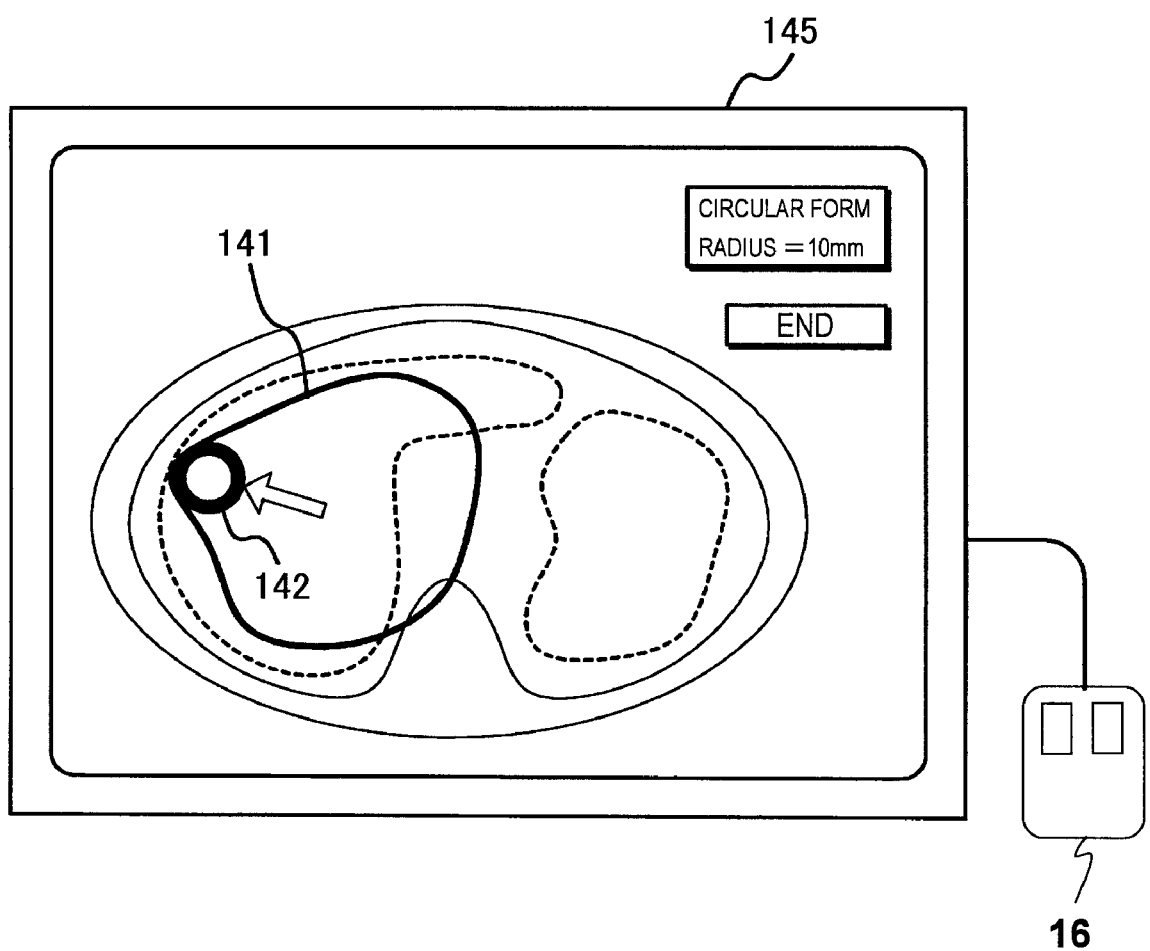
FIG. 4 shows a display example of a terminal image of the processing in FIG. 2.

FIG. 4 shows a display example of the terminal image in the process of FIG. 2, which illustrates the display screen 145 wherein the marker 142 is set inside of the ROI 141 after the marker 142 has been shifted. The marker 142 is set at the position internally touching the ROI 141.

The operator shifts the marker 142 toward the outside direction of the ROI 141 by dragging the mouse 16. The CPU 11 changes the shape of ROI 141 in the vicinity of the contact zone toward outside direction while maintaining the condition that the marker 142 is internally touching the ROI 141. The CPU 11 displays the ROI 141 as well as the marker 142 after being shifted on the display screen 145.

FIG. 5 shows a display example of the processing pattern different from FIG. 3 and FIG. 4 and illustrates the display screen 155 wherein the marker 152a is set on the outside of the ROI 151. FIG. 5(A) shows the marker 152a before being shifted, and FIG. 5(B) shows the marker 152b after being shifted. The marker 152b is set externally touching the ROI 151a.

The operator shifts the marker 152a toward inside direction 153 of the ROI 151a by dragging the mouse 16. The CPU 11 changes the shape of the ROI 151 in the vicinity of the contact zone toward inside direction 153 while maintaining the condition that the marker 152 is touching the ROI 151. The CPU 11 displays the marker 152b after being shifted as well as ROI 151b on the display screen 155.

By proceeding through the above process, the medical image display device changes the shape of an ROI by shifting a marker which is contacting the ROI, and sets the ROI on the contour of the target subject such as an organ.

As a result, it is possible to set an ROI smoothly along the subject, and to accurately extract the subject.

<Example of Changing Shape of a Marker>

Next, an example for changing shape of the marker will be described referring to FIG. 6~FIG. 8.

FIG. 6 shows a display pattern of a marker different from FIG. 3~FIG. 5, illustrating a display screen 165 on which an ROI 161 and a marker 162 are displayed. As shown in FIG. 6(A), the operator expands the size of the marker 162a when curvature radius of an ROI 161a contacting a marker 162a is large. For example, the operator sets the form of the marker 162 as "circular: radius 10 mm" by pushing down a button 166 using the mouse 16.

As shown in FIG. 6(B), the operator reduces the size of the marker 162b when curvature radius of the ROI 161b contacting the marker 162b is small. For example, the operator sets the form of the marker 162b as "circular: radius 5 mm" by pushing down the button 166 using the mouse 16.

Figure 7:
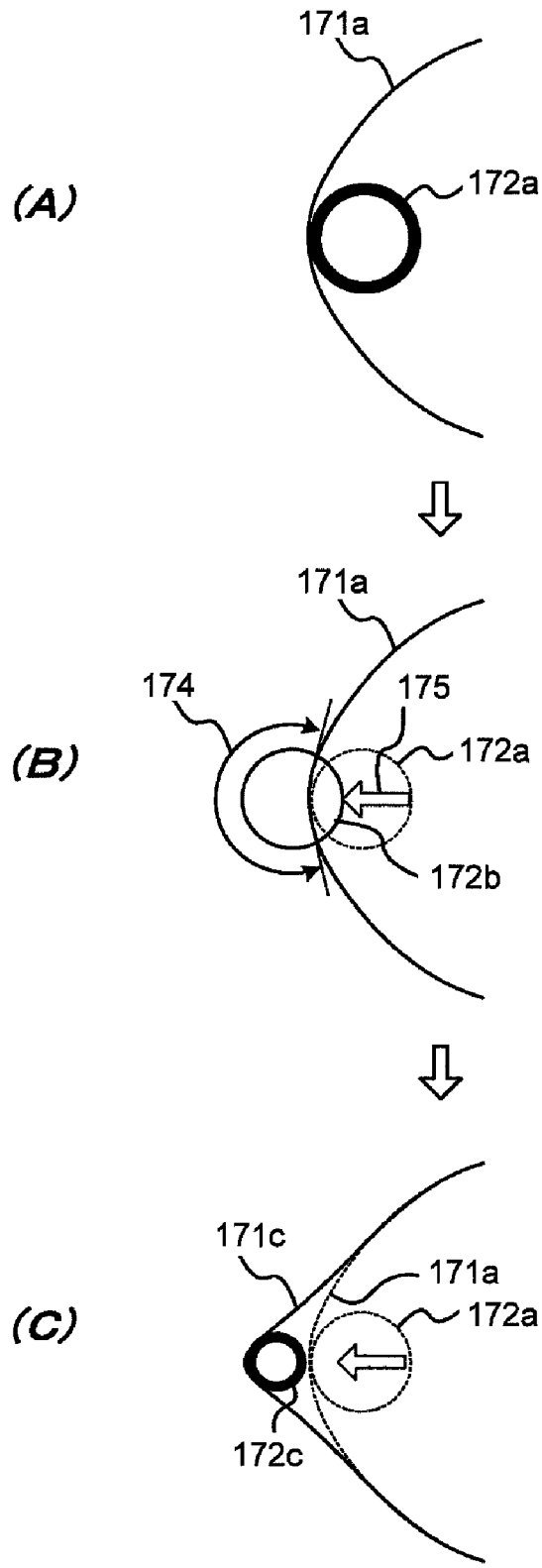
FIG. 7 show a display pattern of a marker different from FIG. 3~FIG. 6.

FIG. 7 shows a display example of the marker different from FIG. 3~FIG. 6 and illustrates the process for changing form of a marker 172.

As for the process for determining the form of the marker step 124 in FIG. 2), as previously described referring to FIG. 6, it may be determined based on the command of the operator. Also, as shown in FIG. 7, it may be set so that the form of the marker is to be automatically set by the CPU 11.

As shown in FIG. 7(A), the CPU 11 displays the ROI 171a and the marker 172a.

As shown in FIG. 7(B), the CPU 11 receives the command for shifting the marker 172, and shifts it to the position of a marker 172b while maintaining the form of the marker 172 as it is. The CPU 11 detects straddle degree of the border between the ROI 171a and the marker 172b. It may be set so that the CPU keeps the marker 172b in the main memory 12 temporally without displaying up to the time that the straddle degree is detected.

As shown in FIG. 7(C), the CPU 11 changes the form of the marker 172 based on the detected straddle degree, and displays the changed marker 172c. For example, it may be set so that the size of the marker 172 is to be made small when the straddle degree is large, and the size of the marker 172 is to be made large when the straddle degree is small. The CPU 11 changes the shape of ROI 171 based on the marker 172c, and displays the ROI 171c.

Straddle degree is a ratio between, for example, a circular-arc length 174 of the marker 172b of the portion protruded outside of the ROI 171a and the circumferential length of the marker 172b. Further, straddle degree may be calculated from the ratio between the circular-arc length 174 and a shifting distance 175. The above-mentioned calculations may be expressed in [Formula 1] below.

(Straddle degree)=(Circular-arc length 174)/(Circumferential length of marker 172b)

(Straddle degree)=(Circular-arc length 174)/(Shifting distance 175)  [Formula 1]

Figure 8:
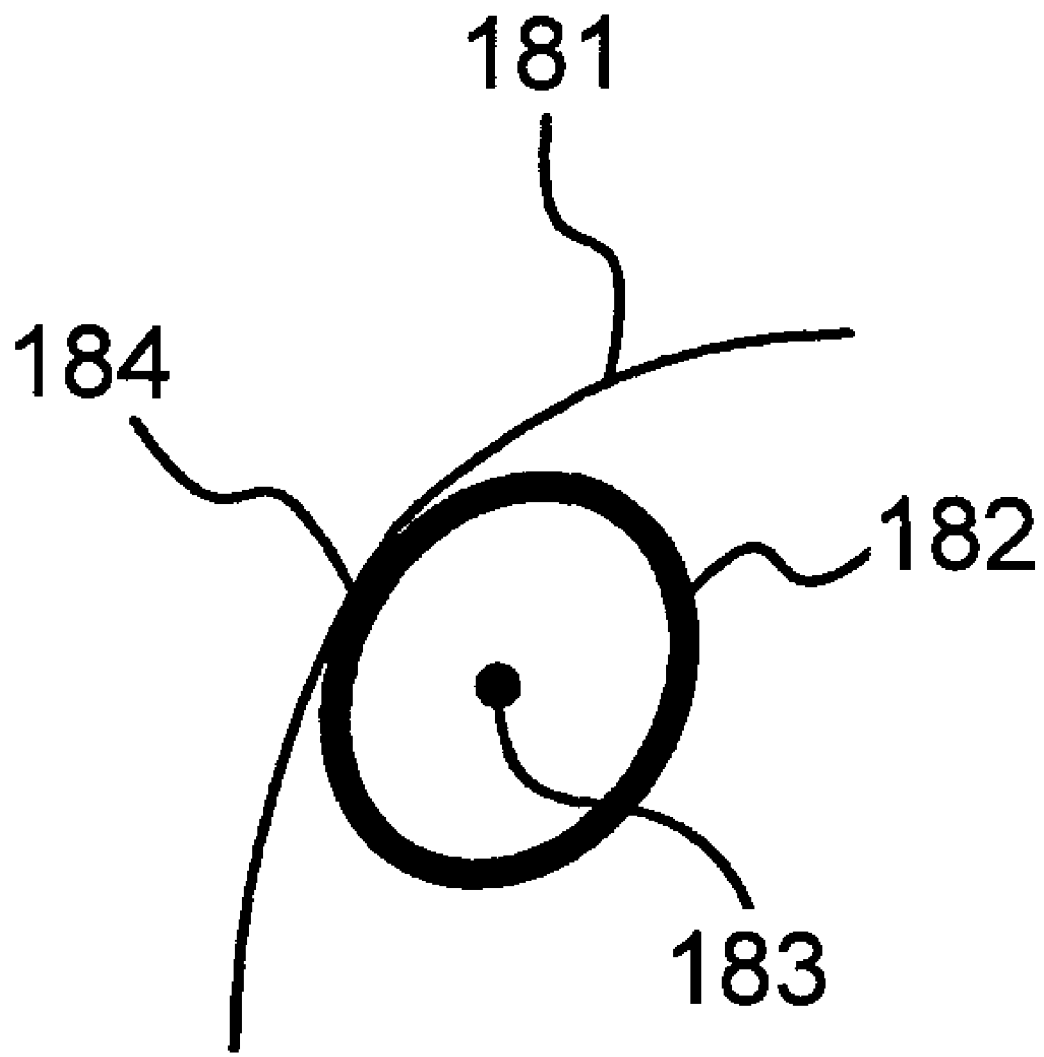
FIG. 8 shows a display pattern of a marker different from FIG. 3~FIG. 7.

FIG. 8 shows a display pattern of a marker different from FIG. 3~FIG. 7, illustrating one illustrative embodiment of a marker 182.

While the shape of the marker is illustrated in circular shape in FIG. 3~FIG. 7, it does not have to be limited to a circular shape. The shape of the marker may be arbitrarily set in accordance with the shape of the subject such as an organ. The shape of the marker 182 shown in FIG. 8 is an ellipse. Further, the major-axis radius and the minor-axis radius of the marker 182 may be set based on the positional relationship between a central position 183 and a contact point 184 and curvature radius of a ROI 181.

When the shape of the marker is circular or ellipse, contour of the organ can be smoothly extracted. The shape of the marker may be other than circular or ellipse shape, such as rectangle or squire. Also, in the case of setting ROI in a very small region such as a blood vessel, the marker may be a "dot".

In this way, by setting a shape of the marker in accordance with the shape of the subject such as an organ or ROI, it is possible to change the shape of the ROI effectively whereby improving the operationality of the display device.

<Program Execution Example 2>

Figure 9:
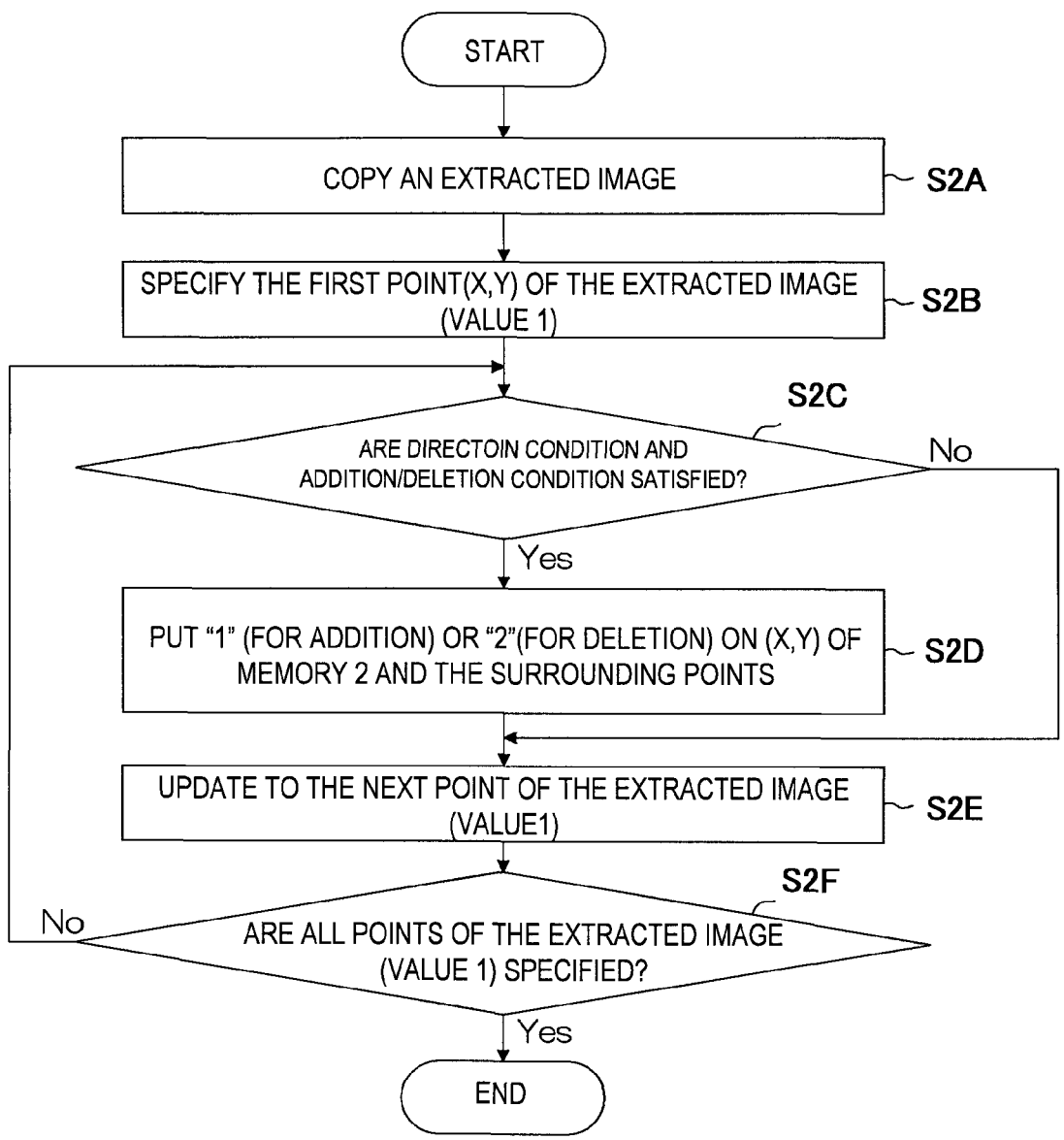
FIG. 9 is a flow chart indicating processing procedure of a program that illustrates other embodiments related to the present invention.

FIG. 9 is a flow chart describing the processing procedure of the program for explaining an embodiment of the present invention, and FIG. 10 shows an example of the screen on which a switch for software for executing the program in FIG. 9 is displayed.

The screen display example of FIG. 10(A) comprises:
  a "direction pixel" icon 21 for displaying a direction pixel setting icon 30 below a medical image 20;
  an "expanding direction" icon 22 for displaying a direction restricting icon to be described later;
  an "ROI setting" icon 23 for specifying the range of a desired region on the medical image 20 by dragging the mouse 16, and setting the specified region as a region of interest (hereinafter referred to as "ROI");
  a number inputting field 24 for inputting numeric value indicating a pixel number (adding pixel number) for one time of expansion in the region growing process;
  a "start addition" icon 25 for executing the process for expanding by the adding pixel number inputted by the number inputting field 24 in one click;
  an "addition of one pixel" icon 26 for executing the region growing process one pixel at a time; and
  an "end" icon 27 for ending the entire process. When the "direction pixel" icon 21 is clicked, the CPU 11 displays the direction pixel setting icon. When the divided region is clicked, the CPU 11 sets the direction coinciding with the clicked divided region as the restricted direction.

Figure 10A:
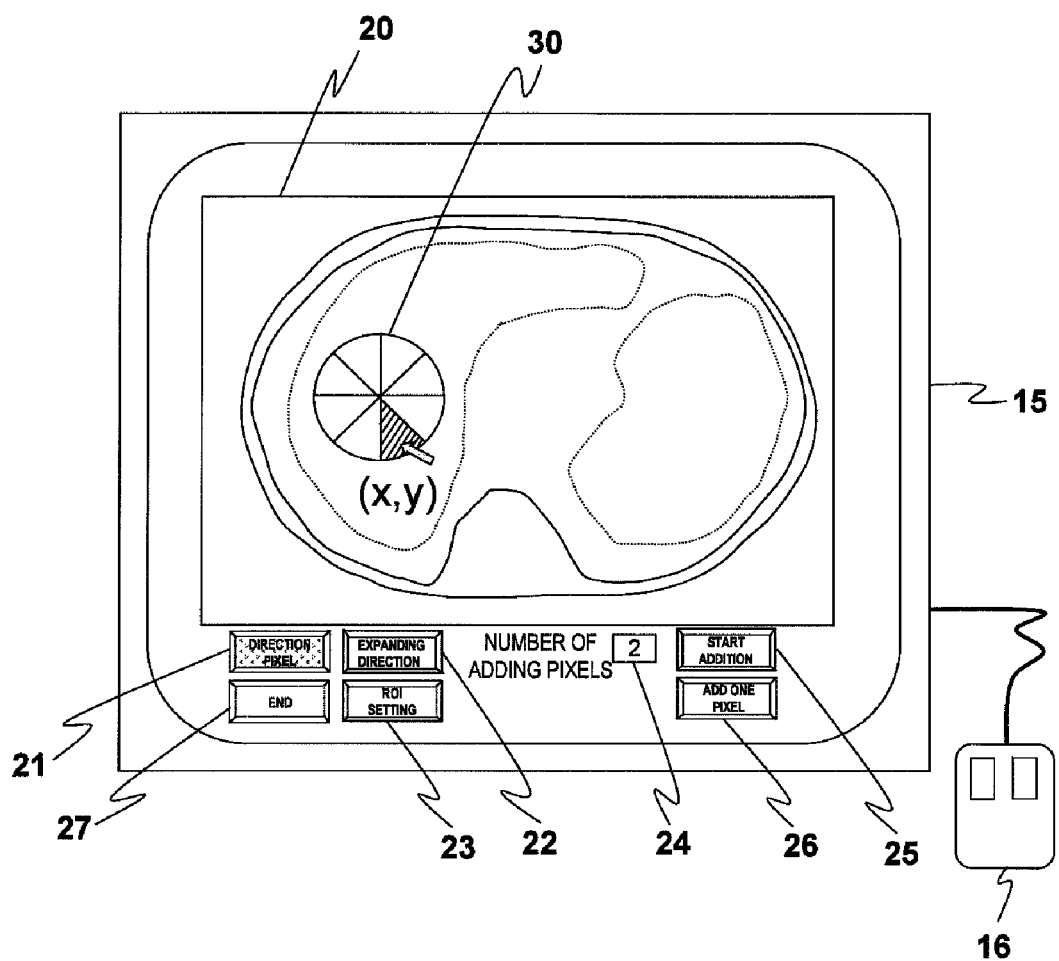
FIG. 10A shows an image display example of a switch for a software to execute the program of FIG. 9.
Figure 10B:
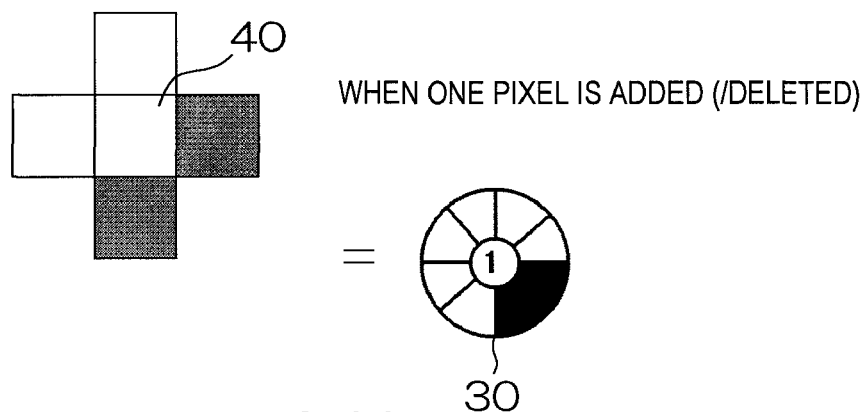
FIG. 10B shows a pattern of an icon illustrated in FIG. 10A.
Figure 10C:
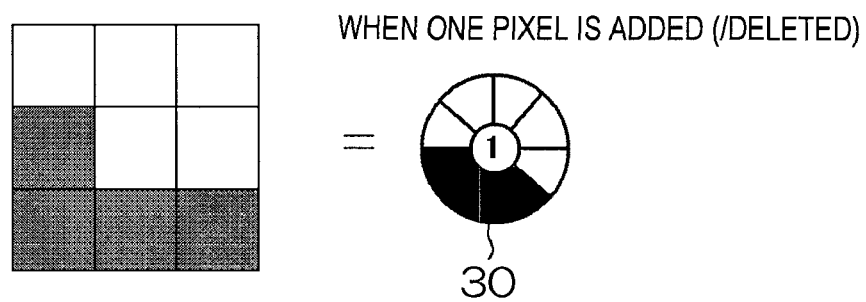
FIG. 10C shows a pattern of an icon different from FIG. 10B.
Figure 10D:
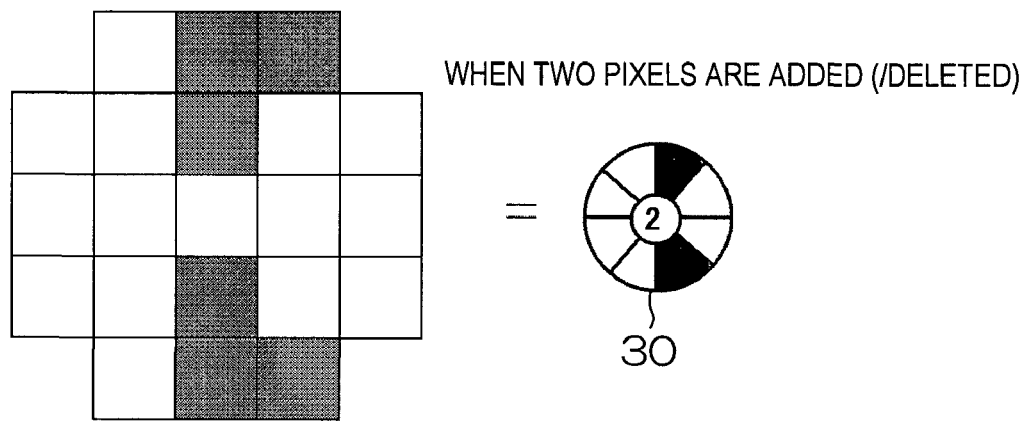
FIG. 10D shows a pattern of an icon different from FIG. 10B and FIG. 10C.

FIG. 10B and FIG. 10C show the case of adding/deleting one pixel, and FIG. 10D shows the case of adding/deleting two pixels. From among the divided regions in the direction pixel setting icon 30, the part displayed in black is the selected divided region.

In FIG. 10B, two divided regions are selected which are in the lower right of the direction pixel setting icon 30. In region expanding/deleting process for expanding/deleting one pixel at a time to upper/lower/right/left direction of a target pixel 40, when the restricting direction is determined by selecting the above-described two divided regions, expanding/deleting direction are restricted to the two pixel (black squares) directions which are on the immediate right and immediate below of the target pixel 40.

In FIG. 10C, three divided regions from the lower right to the lower left of the direction pixel setting icon 30 are selected. In the region expanding/deleting process for expanding/deleting one pixel at a time to eight pixel directions that are adjacent to the target pixel 40, when the restricting direction is determined by selecting the above-described three divided regions, the expanding/deleting directions are restricted in the direction of four pixels (black squares) of immediate lower right, immediate below, immediate lower left and immediate left of the target pixel 40.

In FIG. 10D, two divided regions of one on the lower right together with one on the upper right of the direction pixel setting icon 30 are selected. In the region expanding/deleting process for expanding/deleting two pixels at a time in the direction of eight pixels that are adjacent to the target pixel 40, the expanding/deleting direction is restricted to the three pixel directions (black squares) arranged in "L" shape in downward direction of the target pixel 40 and the three pixel directions (black squares) arranged in reversed "L" shape in upward direction of the target pixel 40 when the restricting direction is determined by selecting the above-described two divided regions.

While the direction pixel setting icon that is circular shape is used above, the shape of the direction pixel setting icon may also be a rectangular shape without being limited to a circular shape. Also, the number of the divided regions does not have to be limited to eight, and an arbitrary number may be set.

Next, execution procedure of the program will be described according to the flow chart in FIG. 9.

The CPU 11 retrieves a medical image (original image) to the display memory 14, extracts a desired region such as an organ based on the threshold value or the region growing method from the retrieved original image, and constructs an extracted image. The CPU 11 records the extracted image in a first area of the main memory 12. The CPU 11 copies the extracted image recorded in the first area of the main memory 12 to a second area. Here, the first area and the second area in the main memory 12 are different areas on the main memory 12 (step S2A).

The operator selects a desired region such as an organ in a medical image. Concretely, if the medical image is in a condition recorded in the display memory 14, the medical image is displayed on a screen 20 of the monitor 15 as shown in FIG. 10(A). The operator selects the desired region such as an organ while observing the above-mentioned screen display by shifting a cursor of the mouse 16 and clicking a button of the mouse 16 so that the cursor is superimposed over the desired region such as an organ.

In this case, the region indicating a liver is selected. The selected region is reflected to the extracted image recorded in the first area, and the first point (x,y) in the extracted image is specified. Accordingly, the first point is set for starting the process. The CPU 11 superimposes the mark for the region expanding process or region deleting process (also referred to as an "icon") 30 locally over a medical image at the position of the specified point (x,y) and displays it on the screen. The icon 30 is referred to as a direction pixel setting icon. The direction pixel setting icon 30 is, for example, circular as an entire shape, and is configured by a plurality of (eight here) divided regions divided into eight directions on the basis of a circular central point. Then the operator shifts the mouse 16 to the divided region being coincided with the desired direction for performing the region expanding process from among the eight divided regions and clicks the region for selecting the region and setting the restricting direction (step S2B).

The CPU 11 determines whether the direction condition is satisfied or not and whether the condition for adding/deleting is satisfied or not (by turning on the button for addition or deletion). When the determination result is "YES", step S2D is carried out. When the result is "NO", step S2E is carried out (step S2C).

For example, the CPU 11 determines "YES" if the addition button, "start addition" icon 25 or "addition of one pixel" icon 26 in FIG. 10A are turned on and the divided region is within the restricted direction regulated by the direction pixel setting icon 30 or the direction restricting icons 60 and 70.

Then "1" is recorded at (x,y) in the second area in the main memory 12 and the surrounding points thereof in the step S2D. Or, the CPU 11 records "0" at (x,y) of the second area in the main memory 12 and the surrounding points thereof, if the delete button not shown in the diagram is turned on and is within the restricting direction (step S2D).

The CPU 11 updates to the next point on the extracted image (value 1). The method for update is to shift one pixel to the right, left, above, below and diagonal of the set pixel (or the previously set number of pixels) (step S2E).

The CPU 11 determines whether all points of the extracted image (value 1) are completed or not. When the determination result is "YES", the process is to be ended. When the result is "NO", step S2C is to be performed again (step S2F).

The direction restricting icon is for restricting the direction for performing the desired process in the same manner as the direction pixel setting icon, but different in shape or specifying method.

<Program Execution Example 3>

Figure 11:
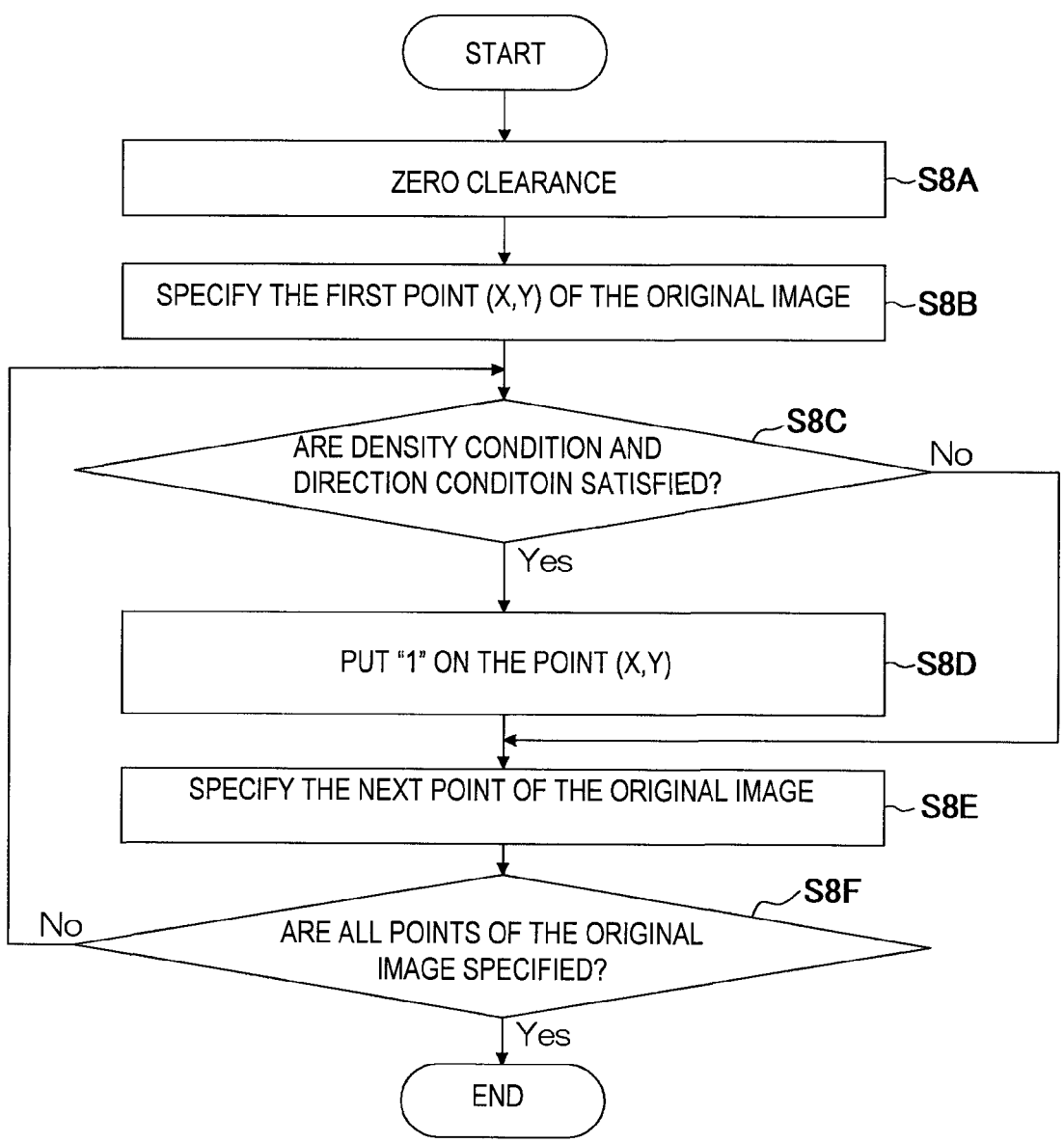
FIG. 11 is a flow chart of a process for region extraction using the region growing process wherein the present invention is applied to an original image.

FIG. 11 is a flow chart illustrating the flow of the process for extracting a region using the region expanding process by applying the present invention with respect to the original image. FIG. 12 is a pattern diagram showing the display content and the result of FIG. 10.

The CPU 11 performs zero clearance on the second area of the main memory 11 (step S8A).

The operator specifies the first point (x,y) of the original image (step S8B).

The CPU 11 reads out the original image to the display memory 14, and displays the original image being read out to the display memory 14 on the monitor 15. The first point of the original image is specified when the target pixel or the direction starting point of the direction pixel setting icon or the direction restricting icon is coincided with the process starting point on the displayed original image by the operator. FIG. 12(A) shows the condition wherein a circular direction pixel setting icon 90 is superimposed and displayed over an original image 91 that is a medical image on which luminal tissues of an object is imaged. The divided region displayed in black in FIG. 12(A) indicates the direction selected as the restricting direction.

The CPU 11 determines whether the density condition and the direction condition are satisfied or not. If the determination result is "YES", the process proceeds to step S8D. If the result is "NO", the process proceeds to step S8E. The density condition here includes the case that the upper limit or lower limit of the density value is set and the pixels having the density value within the set range are extracted, other than the case that the binarization process is performed on the basis of a predetermined threshold, and the pixel having the density value within the set range is extracted (step S8C).

The CPU 11 records "1" on the point of (x,y) of the second area in the main memory 12 (step S8D).

The CPU 11 updates to the next point on the original image (step S8E).

The CPU 11 determines whether all points of the original image are specified or not. If the determination result is "YES", the process is to be ended. If the result is "NO", step S8C is to be carried out again (step S8F).

The expansion result is as shown in FIG. 12(B). That is, as a result of making the position in which the direction pixel setting icon 90 is set in FIG. 12(A) as a starting point and the region expanding process is performed only in the restricting direction indicated by the selected divided regions, only a region 92 which is continuously run in the upper left direction is extracted from the luminal tissues in FIG. 12(B).

Next, the process to perform in the case that the operator desires to also extract the different direction from the first confined direction will be described.

<Program Execution Example 4>

Figure 13:
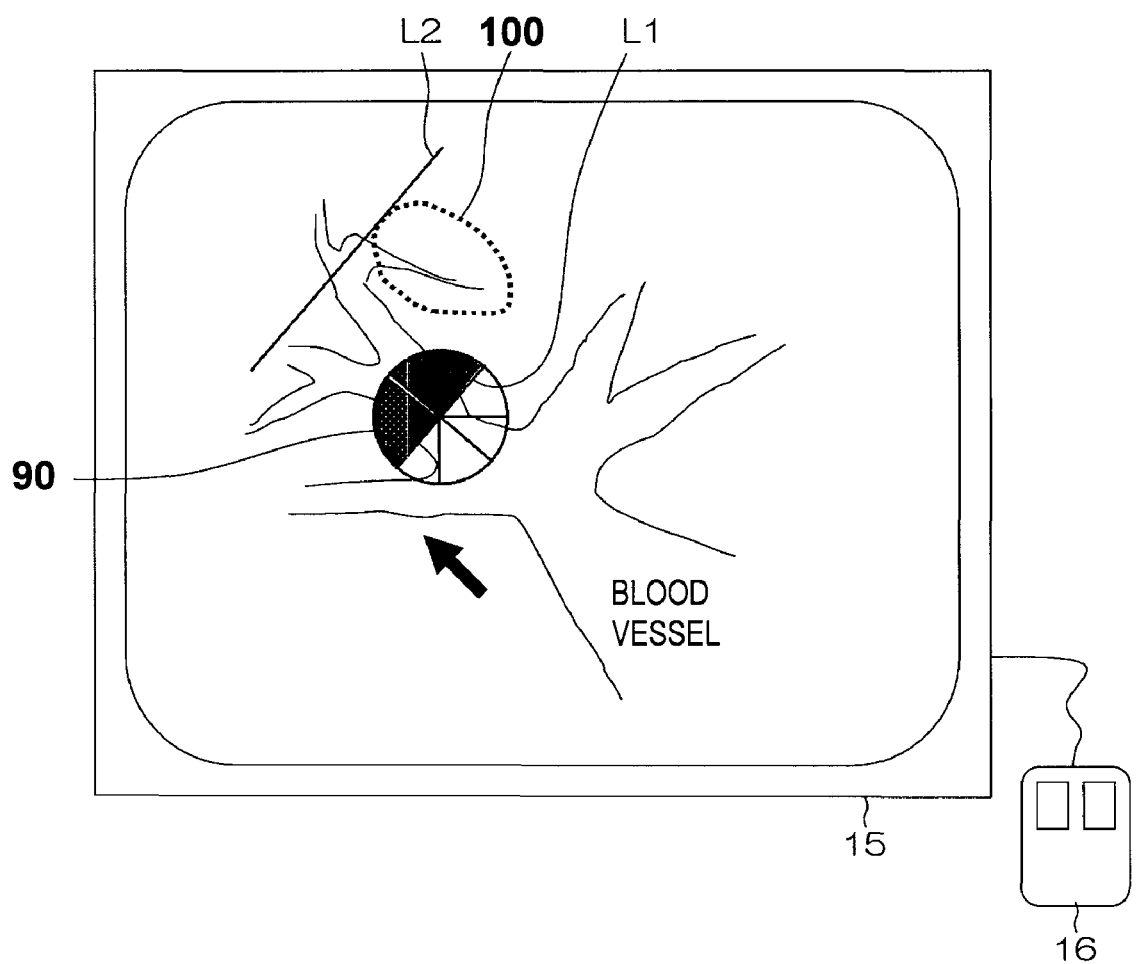
FIG. 13 shows a display example for illustrating the processing for adding a direction with respect to FIG. 12.
Figure 14:
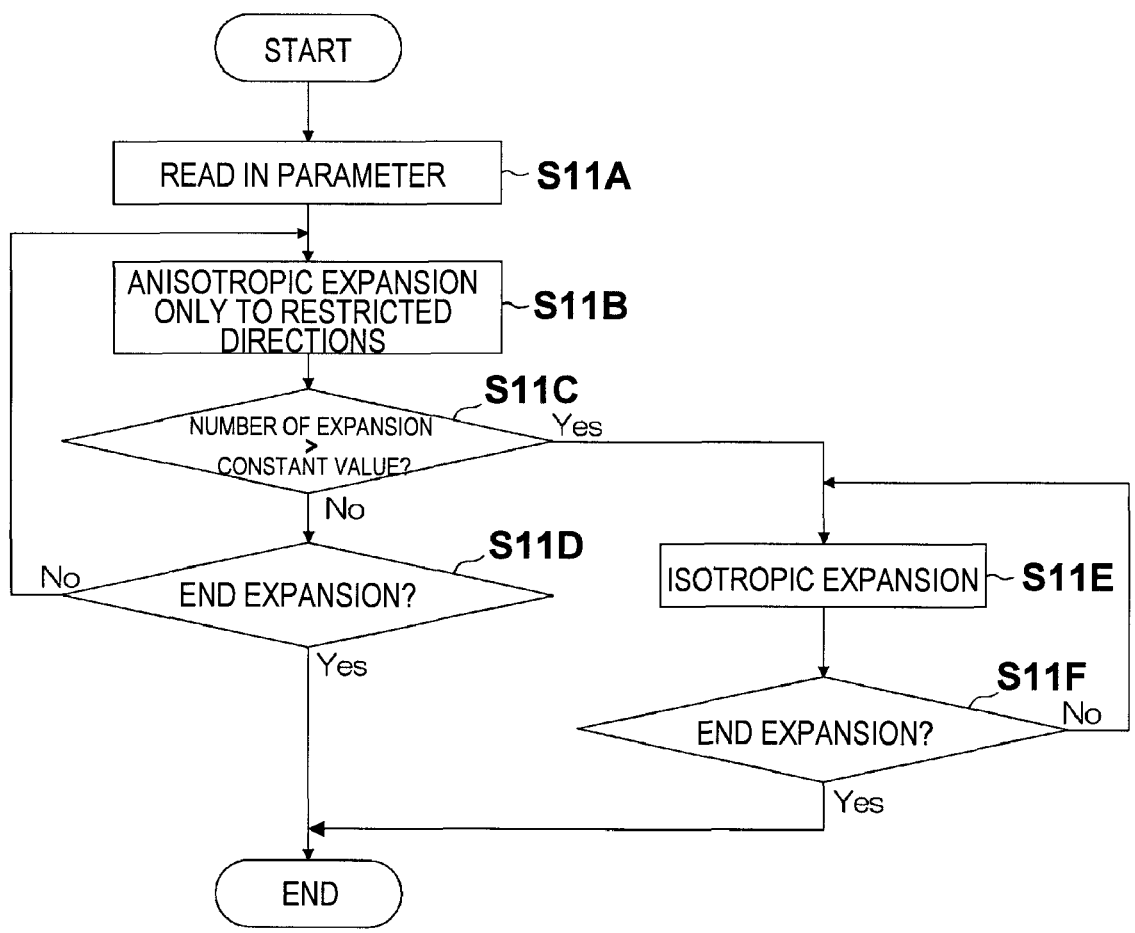
FIG. 14 is a flow chart explaining procedure for adding a direction illustrated in FIG. 13.

FIG. 13 is a display example for illustrating the process with respect to addition of direction, and FIG. 14 is a flow chart illustrating the procedure of direction addition in FIG. 13. As shown in FIG. 13, the luminal tissues encompassed by a dotted line frame 100 (the luminal organ region running over the side of the direction pixel setting icon 90 compared to "L2" which is parallel to a starting line "L1" for regulating the restricting direction of the direction pixel setting icon 90) can not be extracted by the restricting direction which is initially set by the direction pixel setting icon 90. The process for re-extracting the luminal organ within the dotted-line frame 100 will be described according to the flow chart in FIG. 14.

The CPU 11 reads in a parameter such as a number for switching expansion (step S11A).

The CPU performs the region expanding process in anisotropic manner to a restricted direction set by the direction pixel setting icon or the direction restricting icon (step S11B).

The CPU 11 determines whether the inequality "number of expansion>constant value" is applied or not.
If the determination result is "YES", step S11E is carried out.
If the result is "NO", step s11D is carried out (step S11C).

The CPU 11 determines whether the region expanding process is to be ended or not, that is whether there is a pixel that is expanded or not.

If the determination result is "YES", the process is to be ended. If the result is "NO", step S11B is to be performed again (step S11D).

The CPU 11 performs expansion process in isotropic manner (step S11E).

By performing the above-described procedure, the above-described region expanding process can be performed in 360 degrees direction, not only in the restricted directions set by the direction pixel setting icon or the direction restricting icon.

The CPU 11 determines whether the region expanding process is to be ended or not, that is whether there is the expanded pixel or not. If the determination result is 'YES', the process is to be ended. If the result is "NO", step S11E is to be performed again (step S11F).

In the present embodiment, even in the case that there is a region that cannot be expanded in the initially set restricted direction, the region expansion can be performed in isotropic direction following the region expansion to the restricted direction. Particularly, it is possible to improve accuracy of region extraction wherein the expanding direction of the region to be the extraction target is not constant such as luminal organs. While the region expanding process is explained above, the same process can be applied to the region deleting process.

Figure 15:
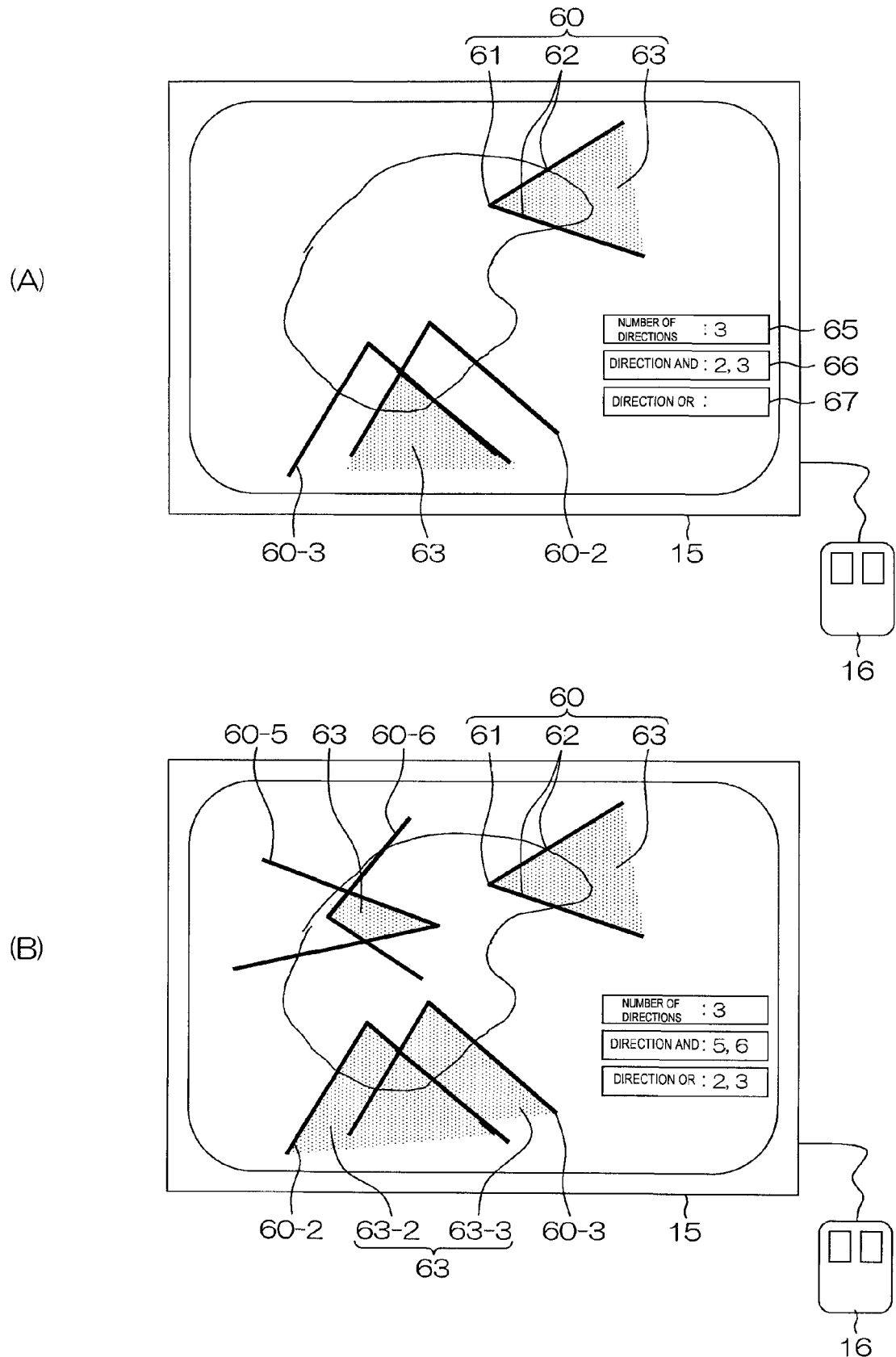
FIG. 15 show patterns of an icon different from FIG. 10A~FIG. 10D.

FIG. 15 shows an icon pattern different from the one in FIG. 10, which is an example of the direction restricting icon. The direction restricting icon 60 is formed by a direction starting point 61 and two line segments (or straight lines) started from the direction starting point 61. The region expanding process or the region deleting process is allowed its process by setting the direction between line segments 62 as a restricted direction 63. In FIGS. 15(A) and (B), the direction starting point 61 is indicated as the intersecting point of the line segments 62, and the restricting direction 63 is displayed using a display color different from the other directions. In the screen of FIG. 15, a "direction number" field 65, "direction AND" field 66 and a "direction OR" field 67 are exemplified. In the "direction number" field 65, the number of the restricting direction is to be inputted. The "direction AND" field 66 specifies a plurality of direction restricting icons 60 when there are a plurality of restricting icons 60, and sets the region (AND) direction on which those restricting directions are overlapped as the restricting direction. The "direction OR" field 67 specifies a plurality of direction restricting icons 60 and sets the direction included in any of the restricting directions (OR direction) as the restricting direction. In FIG. 15(A), "2,3" for specifying the direction restricting icons 60-2, 60-3 are inputted to the "direction AND" field, only AND direction out of the respective restricting directions of the direction restricting icons 60-2, 60-3 are specified as a restricting direction 63.

Such specified restricting direction 63 is set so that the display pattern such as color or luminance of only the region thereof is changed. In the same manner, in FIG. 15(B), when "5,6" for specifying the direction restricting icons 60-5, 60-6 are inputted to the "direction AND" field, only "AND direction" out of the respective restricting directions of the direction restricting icons 60-5, 60-6 is specified as the restricting direction 63. The display pattern of such specified restricting direction 63 is changed only in the region thereof. Also, in FIG. 15(B), when "2,3" for specifying the direction restricting icons 60-2, 63-3 is inputted to the "direction OR" field, "OR direction" of the respective restricting directions 63-2, 63-3 of the direction restricting icons 60-2, 60-3 are specified as the restricting directions 63. The display pattern of such specified restricting direction 63 is changed only in the region thereof. Such specified restricting direction 63 changes the display pattern only in the region thereof. Calculation of the AND direction or the OR direction are performed by the CPU 11.

Figure 16:
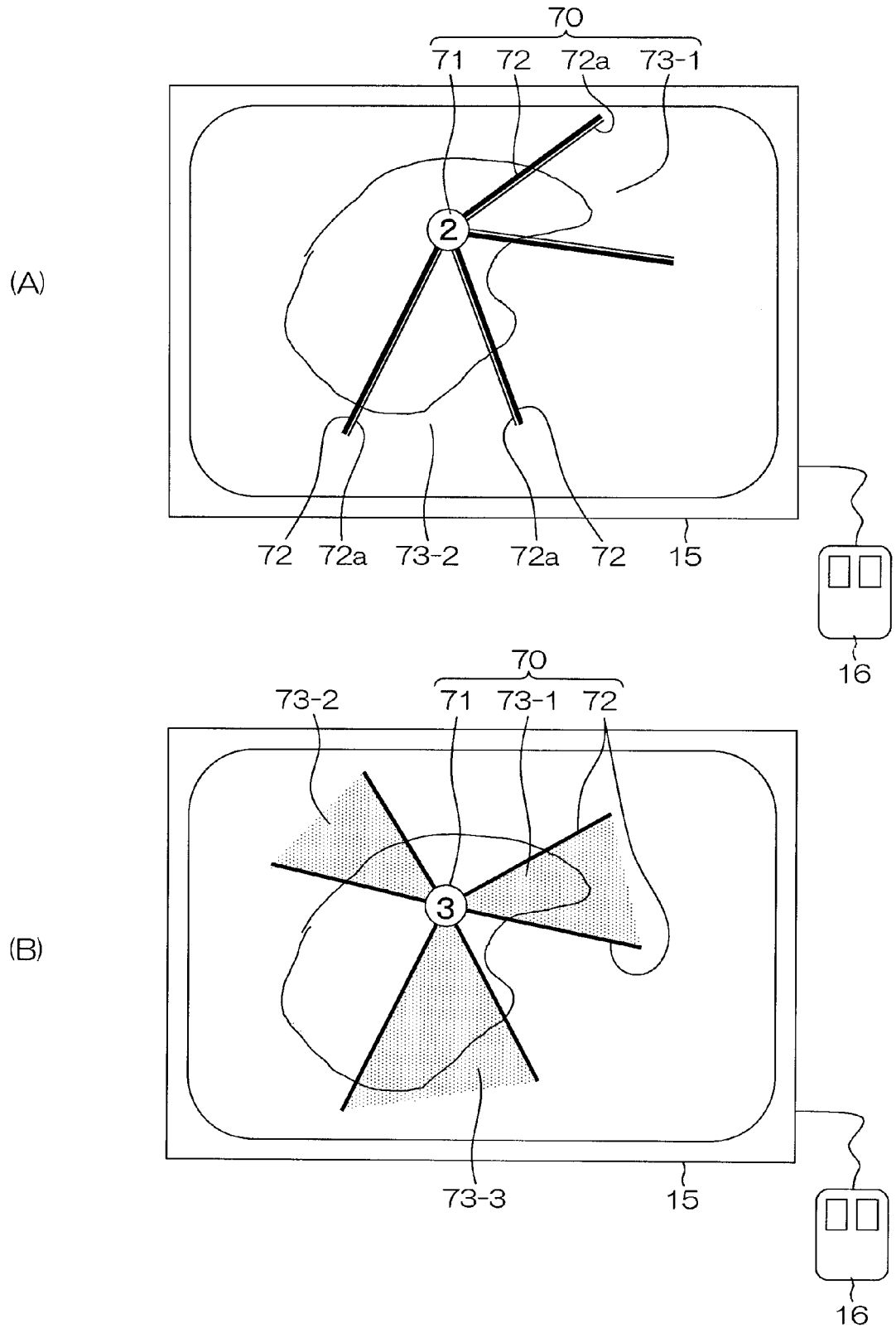
FIG. 16 show another pattern of direction restricting icon in FIG. 14.

FIG. 16 shows another pattern of the direction restricting icon in FIG. 15. A direction restricting icon 70 in FIG. 16 indicates a direction starting point 71 by a circular mark, and number of directions are inputted in the circular mark thereof. For example, in FIG. 16(A), number of the restricting directions is displayed as "2", and number of the restricting directions is displayed as "3" in FIG. 16(B). Then in FIG. 16(A), the restricting directions 73-1, 73-2 are indicated by displaying lines 72a, which are thinner lines than the line segments 72, next to and along two pairs of the two lines of line segments 72 that are extended from the direction starting point 71. Also in FIG. 16(B), three pairs of the two line segments 72 extended from the direction starting point 71 are displayed, and restricting directions 73-1, 73-2, 73-3 are indicated by changing the display color of the region encompassed by those line segments 72.

<Switching Mode>

Figure 17:
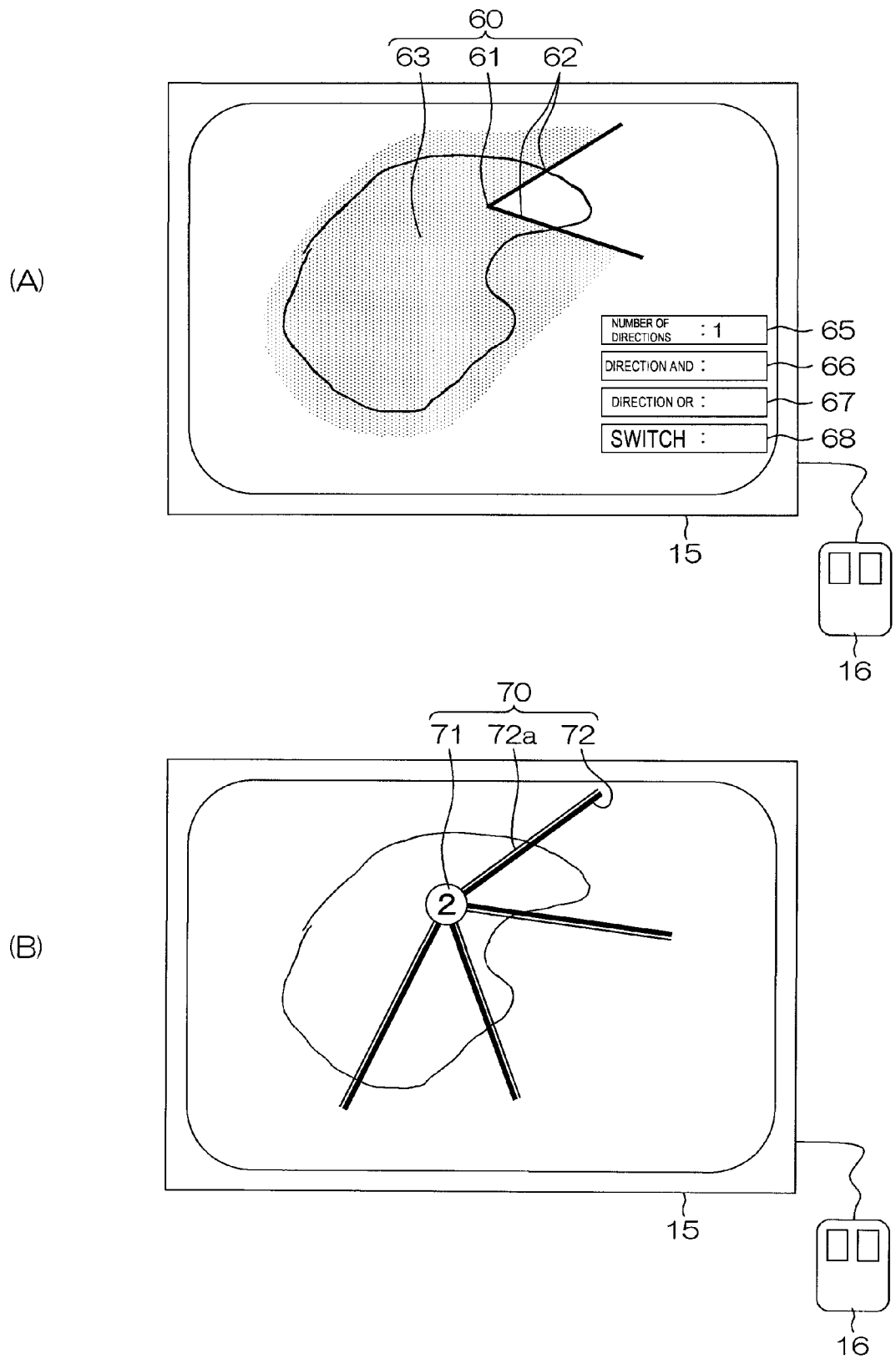
FIG. 17 show an image display example of a process for switching the previously set restricted direction.

FIG. 17 shows an image display example illustrating the process for switching the previously set restricting direction. In FIG. 17(A), a "switch" icon 68 for switching the restricting direction is added and displayed. The direction restricting icon 60 has standard setting so as to display the region larger than 0 degree and smaller than 180 degrees as the restricting direction. When the direction restricting icon 60 is initially displayed, the smaller angle direction out of opened angles of the line segments 62 is to be displayed as the restricting direction 63 as shown in FIG. 15(A). In such condition, by clicking the "switch" icon 68, the setting is changed so as to display the larger angle direction out of the opened angles of the line segments 62 as the restricting direction 63 as shown in FIG. 17(A).

In the same manner, when switching is specified in the direction restricting icon 70 in FIG. 16(A), a line segment 72a is changed and displayed on the outside of the line segment 72 as shown in FIG. 17(B). The switching may be specified by operating the above-mentioned "switch" icon 68 or by shifting the mouse 16 to the display region outside of the line segment 72 and clicking the button of the mouse 16.

<Program Execution Example 5>

Figure 18:
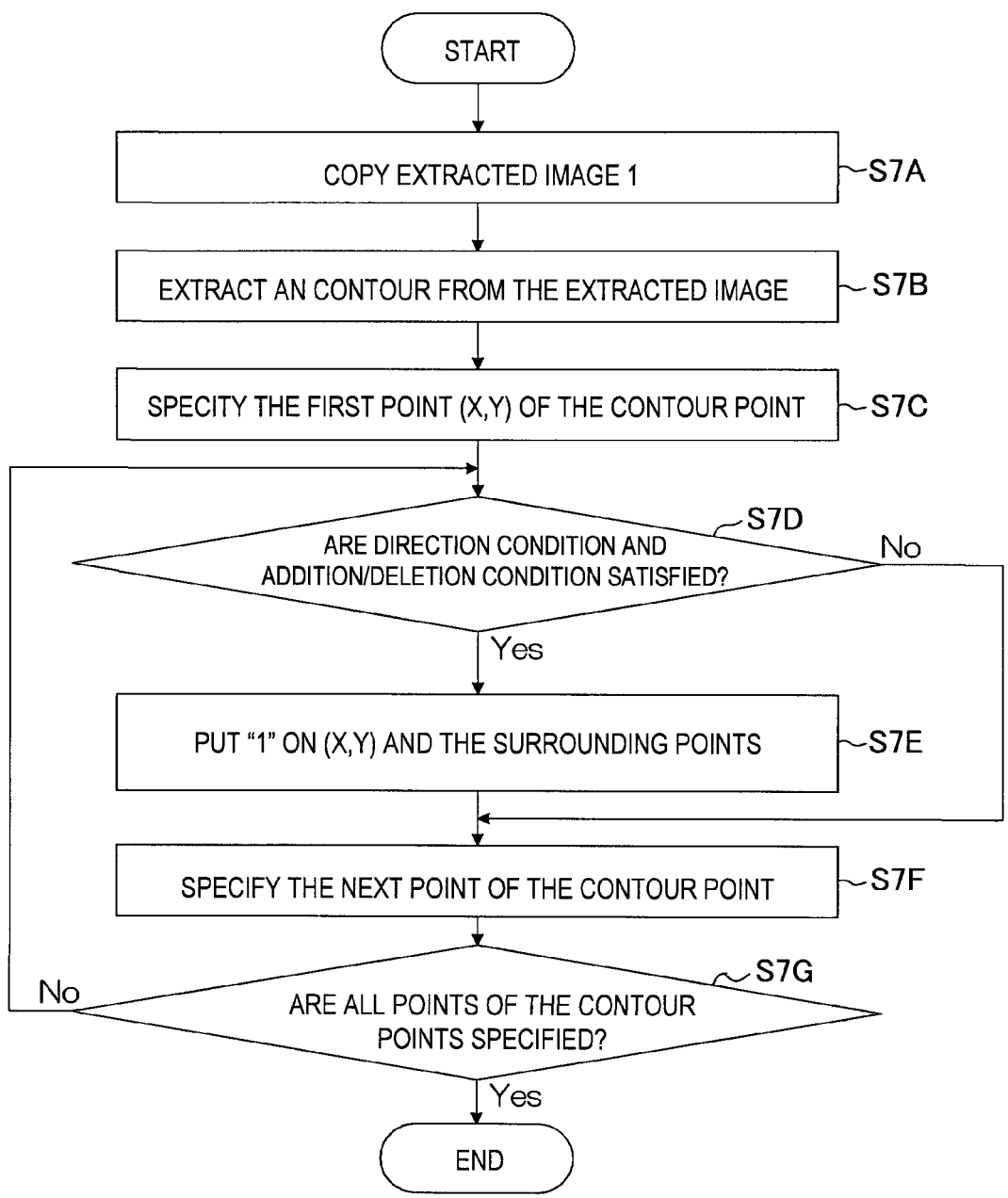
FIG. 18 is a flow chart of the process in the case of applying the present invention to contour points.

FIG. 18 is a flow chart showing the flow of the process in the case of applying the present invention with respect to contour points.

The CPU 11 copies the first area in the main memory 12 in which the extracted image (binary image) is recorded to the second area of the main memory 12 (step S7A).

The CPU 11 performs contour extracting process of the extracted image to be stored in the first area of the main memory 12, and extracts only contour points of the extracted image (binary image) (step S7B).

The operator specifies the first point (x,y) of the contour points. In concrete terms, the operator coincides the center of the direction pixel setting icon (or the target pixel) or the direction starting point of the direction restricting icon with the point for starting the process on a medical image. In this way, the operator can set the first point for the CPU 11 to start the process (step S7C).

The CPU 11 determines whether the direction condition and adding/deleting condition are satisfied or not as in step S2C. If the determination result is "YES", step S7E is carried out. If the result is "NO", step S7F is carried out (step S7D).

The CPU 11 records "1" on (x,y) and the surrounding points thereof in the second area of the main memory 12 (step S7E).

The CPU 11 updates to the next point of the contour points (step S7F).

The CPU 11 determines whether all of the contour points are specified or not. If the determination result is "YES", the process is to be ended. If the result is "NO", step S7D is to be performed again (step S7G).

<The Case of Applying the Present Invention to Volume Data>

In the case of setting the restricting direction in the volume data (3-dimensional data) on which the tomographic images of the object are accumulated, by setting the direction starting point and the restricting direction in a few pieces of the tomographic images, the direction starting point and the restricting direction of the tomographic images between previously mentioned tomographic images may be obtained performing interpolation process without setting the restricting direction for all tomographic images.

Concretely, the CPU 11 juxtaposes and displays an axial image, a sagittal image, a coronal image, a pseudo 3-dimensional image and a 3-dimensional direction restricting icon for setting a 3-dimensional restricting direction. The 3-dimensional direction restricting icon has a function that rotates in accordance with a 3-dimensional image. The operator can set the restricting direction 3-dimensionally by directing addition/deletion direction using the mouse 16 on the rotating axis of the 3-dimensional direction restricting icon. Upon selecting to perform additional (expanding) process or deleting process, the operator is to select one and input using an operation button of an operation panel that is not shown in the diagram.

In accordance with the present embodiment, it is possible to set a restricting direction 3-dimensionally.

<Other Embodiments>

Next, an example will be described for setting an extracting direction of a target region such as an organ by only setting a region of interest.

The CPU 11 automatically calculates the barycenter in the extraction border of a desired region such as an organ, sets the barycenter as the direction starting point based on the barycenter and the ROI set by the operator, and displays the direction restricting icon formed by two line segments passing through the intersecting point of the ROI and the extraction border. By such procedure, the operator can set the restricting direction only by setting an ROI. In the case that this tomographic image is one of the volume images, the obtained range (the direction starting point and the restricting direction which are regulated by the direction restricting icon) may be applied to other tomographic images using interpolation process.

Also, the restricting direction may be set by combining the direction pixel setting icon and the direction restricting icon. In other words, the desired restricting direction to be set is indicated by the overlapped (AND) direction of the restricting direction indicated by the direction restricting icon and the restricting direction indicated by the direction pixel setting icon. The direction starting point is the apex of the direction restricting icon, and the barycenter of the extracting region indicated by the extraction border.

While "AND" and "OR" are cited as an example for specifying the restricting direction by combining the direction pixel setting icon and the direction restricting icon, or a plurality of direction restricting icons, the combination of the directions indicated by the respective icons may be set arbitrarily using the combination of logical symbols such as "NAND", "NOR" other than "AND", "OR".

While preferred embodiments of the medical image display device related to the present invention are described above referring to the attached diagrams, as will be understood by those skilled in the art, no limitations are intended to the particular forms described, and the intension is to cover all modifications, equivalents, and alternatives falling within the spirit and scope of the disclosed technical idea of the present invention.

The invention claimed is:

1. A medical image display device comprising:
  setting means for setting first reference information for starting the extraction of a desired region on a medical image displayed on display means and second reference information for terminating the region extraction; and
  control means for generating a marker with finite size indicating execution information of the region extracting process in the direction from the first reference information to the second reference information set by the setting means, and controls display of the marker and a region of interest on the display means by associating it with the medical image, wherein
  the setting means shifts and sets the marker, and
  the control means changes the shape of the region of interest so as to contact the marker after the marker is shifted.

2. The medical image display device according to claim 1, wherein the control means extends the region of interest, and the marker, after being shifted, internally touches the region of interest.

3. The medical image display device according to claim 1, wherein the control means reduces the region of interest, and the marker, after being shifted, externally touches the region of interest.

4. The medical image display device according to claim 1, wherein:
the setting means variably sets size or shape of the marker; and
the control means variably changes the size and shape of the region of interest based on the marker variably set by the setting means.

5. The medical image display device according to claim 1, wherein the setting means further sets information on addition/deletion of the region extracting process as the execution information of the process thereof.

6. The medical image display device according to claim 1, wherein the control means arranges the center of the marker at the position of the first reference information, sets the shape of the marker as a circular or rectangular shape so as to be able to extend the region extracting process in a plurality of directions including the direction from the first reference information to the second reference information, and generates mark information of the shape thereof.

7. The medical image display device according to claim 6, wherein the setting means further sets the pixel number for executing addition or deletion of the region extracting process on the marker displayed on the display means.

8. The medical image display device according to claim 1, wherein:
the setting means sets the information of the direction from the first reference information to the second reference information as first direction information, and further sets second direction information different from the first direction information; and
the control means generates the marker based on the first direction information and the second direction information set by the setting means.

9. The medical image display device according to claim 1, wherein the setting means sets information on the number of directions of the region extracting process on the marker displayed on the display means.

10. The medical image display device according to claim 1, wherein:
the setting means sets information on logical operation with respect to marker for each direction number as well as setting a plurality of direction number of the region extracting process; and
the control means generates the marker based on each piece of information of the direction number and logical operation of the set region extracting process.

11. The medical image display device according to claim 1, wherein:
the setting means sets a plurality of line segments corresponding to the direction number of the region extracting process; and
the control means generates the marker based on the set plurality of line segments.

12. The medical image display device according to claim 1, wherein:
the setting means sets switching information from a plurality of the process patterns of the region extracting process; and
the control means generates the marker based on the set switching information.

13. The medical image display device according to claim 1, wherein the control means generates the marker based on contour information of the region wherein the region extracting process is performed.

14. The medical image display device according to claim 1, wherein the control means generates the marker based on pixel information of an original image of the region wherein the region extracting process is performed.

15. A medical image display program of instructions executable by a computer for causing the computer to perform:
a setting function for setting first reference information for starting extraction of a desired region on a medical image displayed on a monitor and second reference information for terminating the region extraction; and
a control function for generating a marker with finite size indicating execution information of the region extracting process in the direction from the set first reference information to the second reference information, and controlling display of the marker and a region of interest on the monitor associating it with the medical image, wherein
the setting function shifts and sets the marker, and
the control function changes the shape of the region of interest so as to contact the marker after the marker is shifted.

* * * * *